(12) United States Patent
Chin et al.

(10) Patent No.: US 10,639,016 B2
(45) Date of Patent: May 5, 2020

(54) METHODS AND DEVICES FOR FALLOPIAN TUBE DIAGNOSTICS

(71) Applicant: nVISION MEDICAL CORPORATION, San Francisco, CA (US)

(72) Inventors: Albert Chin, San Francisco, CA (US); Surbhi Sarna, San Francisco, CA (US); David W. Snow, San Francisco, CA (US); Jesus Magana, San Francisco, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 495 days.

(21) Appl. No.: 15/053,568

(22) Filed: Feb. 25, 2016

(65) Prior Publication Data

US 2016/0278747 A1   Sep. 29, 2016

Related U.S. Application Data

(63) Continuation-in-part of application No. 14/764,710, filed as application No. PCT/US2014/014472 on Feb. 3, 2014.

(Continued)

(51) Int. Cl.
*A61B 10/02* (2006.01)
*A61M 25/10* (2013.01)
(Continued)

(52) U.S. Cl.
CPC ...... *A61B 10/0291* (2013.01); *A61B 17/1204* (2013.01); *A61B 17/12099* (2013.01);
(Continued)

(58) Field of Classification Search
None
See application file for complete search history.

(56) References Cited

U.S. PATENT DOCUMENTS 2,701,559 A   2/1955   Cooper
3,168,092 A   2/1965   Silverman
(Continued)

FOREIGN PATENT DOCUMENTS

DE   3331813 A1   3/1985
EP   0227583 A2   7/1987
(Continued)

OTHER PUBLICATIONS

Extended Search Report from European Patent Office dated Jun. 13, 2016 for application No. PCT/US2014/014472.
(Continued)

*Primary Examiner* — Sean P Dougherty
*Assistant Examiner* — Benjamin S Melhus

(57) ABSTRACT

Methods and devices for performing minimally invasive procedures useful for Fallopian tube diagnostics are disclosed. In at least one embodiment, the proximal os of the Fallopian tube is accessed via an intrauterine approach; an introducer catheter is advanced to cannulate and form a fluid tight seal with the proximal os of the Fallopian tube; a second catheter inside the introducer catheter is provided to track the length of the Fallopian tube and out into the abdominal cavity; a balloon at the end of the second catheter is inflated and the second catheter is retracted until the balloon seals the distal os of the Fallopian tube; irrigation is performed substantially over the length of the Fallopian tube; and the irrigation fluid is recovered for cytology or cell analysis.

16 Claims, 16 Drawing Sheets

Related U.S. Application Data

(60) Provisional application No. 61/873,753, filed on Sep. 4, 2013, provisional application No. 61/759,783, filed on Feb. 1, 2013.

(51) Int. Cl.
*A61M 25/01* (2006.01)
*A61B 1/303* (2006.01)
*A61B 90/00* (2016.01)
*A61B 17/12* (2006.01)
*A61B 17/42* (2006.01)

(52) U.S. Cl.
CPC . *A61B 17/12136* (2013.01); *A61B 2017/4233* (2013.01); *A61B 2090/392* (2016.02); *A61B 2090/3966* (2016.02); *A61B 2090/3987* (2016.02); *A61B 2217/007* (2013.01)

(56) References Cited

U.S. PATENT DOCUMENTS

| | | | |
|---|---|---|---|
| 3,500,819 | A | 3/1970 | Silverman |
| 3,664,328 | A | 5/1972 | Moyle, Jr. et al. |
| 4,157,709 | A | 6/1979 | Schuster et al. |
| 4,324,262 | A | 4/1982 | Hall |
| 4,467,816 | A | 8/1984 | Schlueter et al. |
| 4,946,440 | A | 8/1990 | Hall |
| 5,163,927 | A | 11/1992 | Woker et al. |
| 5,171,305 | A | 12/1992 | Schickling et al. |
| 5,374,247 | A | 12/1994 | Lowery et al. |
| 5,738,109 | A | 4/1998 | Parasher |
| 5,762,069 | A | 6/1998 | Kelleher et al. |
| 6,383,805 | B1 | 5/2002 | Latimer |
| 6,478,807 | B1 * | 11/2002 | Foreman ............... A61F 2/958 606/108 |
| 6,840,946 | B2 | 1/2005 | Fogarty et al. |
| 7,255,687 | B2 | 8/2007 | Huang et al. |
| 8,470,043 | B2 | 6/2013 | Schaller et al. |
| 8,652,067 | B2 | 2/2014 | Lonky et al. |
| 8,747,352 | B1 | 6/2014 | Lalonde |
| 9,028,401 | B1 | 5/2015 | Bacich et al. |
| 9,161,773 | B2 | 10/2015 | Schaller et al. |
| 9,282,951 | B2 | 3/2016 | Lonky et al. |
| 9,320,502 | B2 | 4/2016 | Osullivan et al. |
| 9,492,570 | B2 | 11/2016 | Sirimanne et al. |
| 9,493,839 | B2 | 11/2016 | Speiser et al. |
| 2001/0029044 | A1 | 10/2001 | Gombrich et al. |
| 2003/0014069 | A1 | 1/2003 | Fogarty et al. |
| 2003/0040754 | A1 * | 2/2003 | Mitchell ............... A61F 2/07 606/106 |
| 2003/0055373 | A1 | 3/2003 | Sramek et al. |
| 2003/0208223 | A1 | 11/2003 | Kleiner |
| 2004/0030263 | A1 | 2/2004 | Dubrul et al. |
| 2004/0116827 | A1 | 6/2004 | Tiberio |
| 2005/0021069 | A1 | 1/2005 | Feuer et al. |
| 2005/0245876 | A1 | 11/2005 | Khosravi et al. |
| 2006/0079924 | A1 | 4/2006 | Sanders et al. |
| 2009/0005754 | A1 | 1/2009 | Soetermans |
| 2009/0254063 | A1 | 10/2009 | von Oepen et al. |
| 2010/0234726 | A1 | 9/2010 | Sirimanne et al. |
| 2011/0066099 | A1 | 3/2011 | Hoskins |
| 2011/0172557 | A1 | 7/2011 | Lonky et al. |
| 2012/0197157 | A1 | 8/2012 | Ryan et al. |
| 2012/0259401 | A1 | 10/2012 | Gerrans et al. |
| 2012/0315662 | A1 | 12/2012 | Linnemeier |
| 2013/0172778 | A1 | 7/2013 | Teschendorf |
| 2013/0267870 | A1 | 10/2013 | Lonky |
| 2013/0338533 | A1 | 12/2013 | Olsen |
| 2014/0128732 | A1 | 5/2014 | Roy et al. |
| 2014/0257098 | A1 | 9/2014 | Del Priore |
| 2015/0005781 | A1 | 1/2015 | Lund-Clausen et al. |
| 2015/0057565 | A1 | 2/2015 | Mazzoli, Jr. et al. |
| 2015/0133737 | A1 | 5/2015 | Bacich et al. |
| 2015/0351729 | A1 | 12/2015 | Chin et al. |
| 2017/0354437 | A1 | 12/2017 | Bacich |
| 2018/0014773 | A1 | 1/2018 | Barton et al. |

FOREIGN PATENT DOCUMENTS

| | | |
|---|---|---|
| EP | 0539084 A1 | 4/1993 |
| JP | S53139397 A | 12/1978 |
| JP | S5532576 A | 3/1980 |
| JP | H01131641 A | 5/1989 |
| JP | H0621607 U | 3/1994 |
| JP | H09108227 A | 4/1997 |
| JP | 2003527900 A | 9/2003 |
| JP | 2003530900 A | 10/2003 |
| JP | 2006043412 A | 2/2006 |
| JP | 2008505672 A | 2/2008 |
| JP | 2011156379 A | 8/2011 |
| WO | 9611372 A1 | 4/1996 |
| WO | 0170297 A2 | 9/2001 |
| WO | 2003018085 A2 | 3/2003 |
| WO | 2007146061 A2 | 12/2007 |
| WO | 2009142605 A1 | 11/2009 |
| WO | 2010033467 A1 | 3/2010 |
| WO | 2010081000 A1 | 7/2010 |
| WO | 2015070095 A1 | 5/2015 |
| WO | 2015089422 A1 | 6/2015 |

OTHER PUBLICATIONS

International Search Report dated Jun. 5, 2017 for International Application No. PCT/US2017/019700 filed Feb. 27, 2017.
Kurman RJ et al. The origin and pathogenesis of epithelial ovarian cancer; a proposed unifying theory. Am J Surg Pathol. 2010, 34 (3), pp. 433-443. doi: 10.1097/PAS.0b013e3181cfd79.
Mulvany J.N. et al. Fallopian tube cytology: a histocorrelative study of 150 washings. Dign. Cytopathol. 1997, 16 (6), p. 483-438.
Extended European Search Report for Application No. 17757421.7, dated Sep. 26, 2019, 7 pages.
Supplementary European Search Report for Application No. EP14745577.8, dated Jun. 13, 2016, 7 pages.
International Search Report and Written Opinion for International Application No. PCT/US2017/019700 dated Jun. 5, 2017, 11 pages.

* cited by examiner

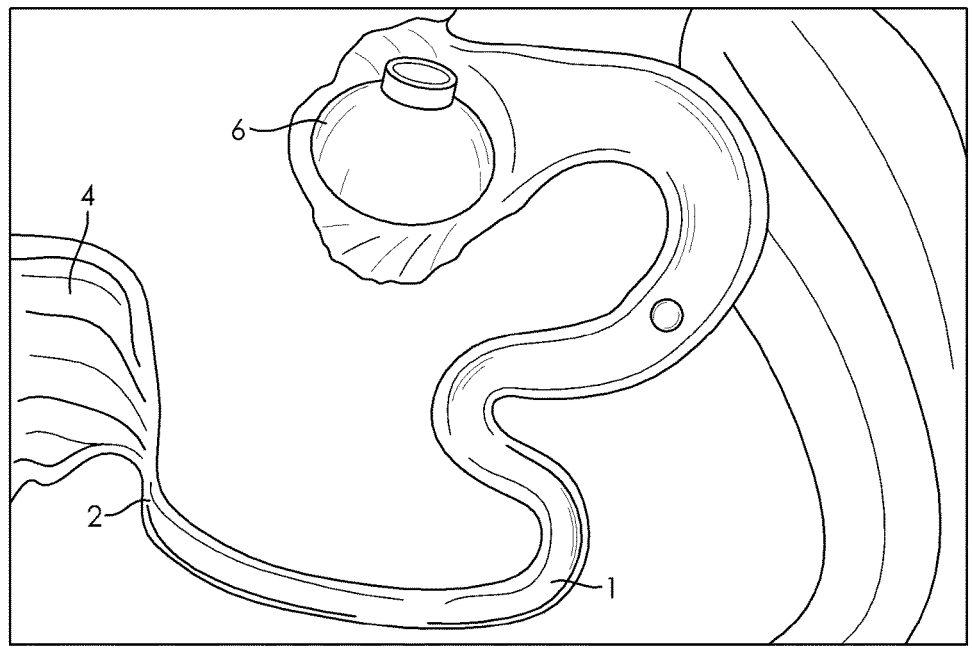
**FIG.1
PRIOR ART**
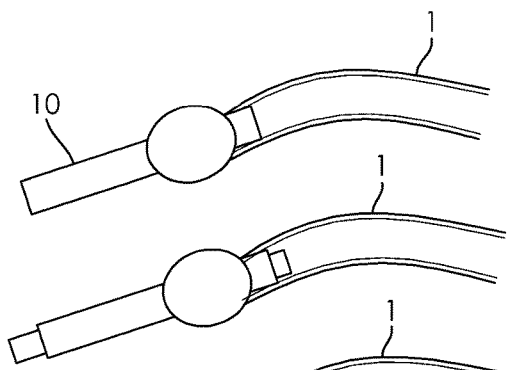
FIG. 2A
FIG. 2B
FIG. 2C
FIG. 2D

METHODS AND DEVICES FOR FALLOPIAN TUBE DIAGNOSTICS

RELATED APPLICATIONS

This application is a continuation-in-part of U.S. patent application Ser. No. 14/764,710 filed Jul. 30, 2015; that in turn claims priority benefit of PCT/US14/14472 filed Feb. 3, 2014 that in turn claims priority benefit of U.S. Provisional Application Ser. No. 61/873,753 filed Sep. 4, 2013, and U.S. Provisional Application Ser. No. 61/759,783 filed Feb. 1, 2013; the contents of the aforementioned applications are hereby incorporated by reference in their entirety and incorporates the disclosure thereof in its entirety.

FIELD OF THE INVENTION

The present invention in general relates to Fallopian tube diagnostics and in particular to a catheter and diagnostic collection devices that accommodate the anatomical difficulties associated with navigation within the Fallopian tube.

BACKGROUND OF THE INVENTION

Ovarian cancer is a significant disease in women; 1 out of 72 women in the U.S. is diagnosed with ovarian cancer sometime during her lifetime. In 2012, 22,280 women in the U.S. were diagnosed with this illness, and 15,500 women died of this malignancy. Ovarian cancer is disproportionately deadly because this type of cancer lacks any clear early detection or screening test, meaning that most cases of ovarian cancer are not diagnosed until they have reached advanced stages. Thus, ovarian cancer screening is of high clinical interest because the disease is not typically detectable at its early stages, when it is the most curable.

Definitive detection of ovarian cancer presently requires a surgical procedure to obtain cell samples for diagnosis. Since the ovaries are intra-abdominal, laparoscopic or open surgery (laparotomy) must be performed to access the ovaries for evaluation. Furthermore, biopsy of the ovary is not generally recommended by medical guidelines as there exists a risk of spreading the cancer further.

Anatomically, the ovaries are in close proximity of the fimbria at the region of the distal opening or os of the Fallopian tube. Eggs released by the ovary are gathered by the fimbria and transported through the Fallopian tube to the uterus. In ovarian cancer, cells may be deposited in the Fallopian tube; a few of these cells may find their way into the uterus. Cell samples obtained from the uterus may detect ovarian malignancy; however, the incidence of migration of ovarian cancer cells into the uterus is too low to render uterine sampling a reliable diagnostic test for ovarian malignancy. A higher number of ovarian cancer cells migrate to the Fallopian tube; this number increases in the distal portion of the tube, near the distal os. The ability to test cells in the Fallopian tube for malignancy would be of considerable clinical value for the early detection and treatment of such cancers, if such could be performed without concern about spreading cancerous cells. Additionally, a need exists to distinguish ovarian cancers from Fallopian tube cancers based on the finding of abnormal cells in the Fallopian tubes for several reasons including the varying treatment regimens therebetween.

However, the introduction of a diagnostic device into the Fallopian tube is problematic since the Fallopian tube is extremely fragile and prone to perforation during passage of most devices. Perforation generally occurs at the uterotubal junction (UTJ), a constriction that occurs approximately 1 cm distal to the proximal os (opening) of the Fallopian tube in the uterus. The lumen size at this constriction may be as small as 0.3 mm or 0.5 mm, while the lumen size of the Fallopian tube adjacent to the uterotubal junction is approximately 1 mm. FIG. 1 depicts a cross-sectioned view of the Fallopian tube 1 with the uterotubal junction (UTJ) 2 that connects the uterus 4 to the ovaries 6.

Thus, there exists a need for a device and process to allow cell samples to be obtained from Fallopian tube for evaluation of ovarian cancer in a minimally invasively fashion and, particularly without the need for a skin incision. There further exists a need for securing a sample of representative cells from the Fallopian tube with a catheter to screen for early stage cancers

SUMMARY OF THE INVENTION

Methods and devices for performing minimally invasive procedures useful for Fallopian tube diagnostics are disclosed. In at least one embodiment, the proximal os of the Fallopian tube is accessed via an intrauterine approach; an introducer catheter is advanced to cannulate and form a fluid tight seal with the proximal os of the Fallopian tube; a second catheter inside the introducer catheter is provided to track the length of the Fallopian tube and out into the abdominal cavity; a balloon at the end of the second catheter is inflated and the second catheter is retracted until the balloon seals the distal os of the Fallopian tube; irrigation is performed substantially over the length of the Fallopian tube; and the irrigation fluid is recovered for cytology or cell analysis.

BRIEF DESCRIPTION OF THE DRAWINGS

The present invention is further detailed with respect to the following non-limiting specific embodiments of the present invention. The appended claims should not be construed as being limited to the specific devices so detailed.

FIG. 1 depicts a prior art cross-sectioned view of a Fallopian tube with the uterotubal junction (UTJ) that connects the uterus to the ovaries;

FIGS. 2A-2D are schematic, cross-sectional side views that depict the sequential insertion of a specific embodiment of an invention catheter into a Fallopian tube insertion catheter to seal against a Fallopian tube end (A); an everting sleeve catheter is inserted through insertion catheter into the tube (B); a distal balloon is inflated as the sleeve is extended (C); and (D) irrigation is deployed to remove cells from the Fallopian tube lumen wall;

DETAILED DESCRIPTION OF THE INVENTION

Figure 3:
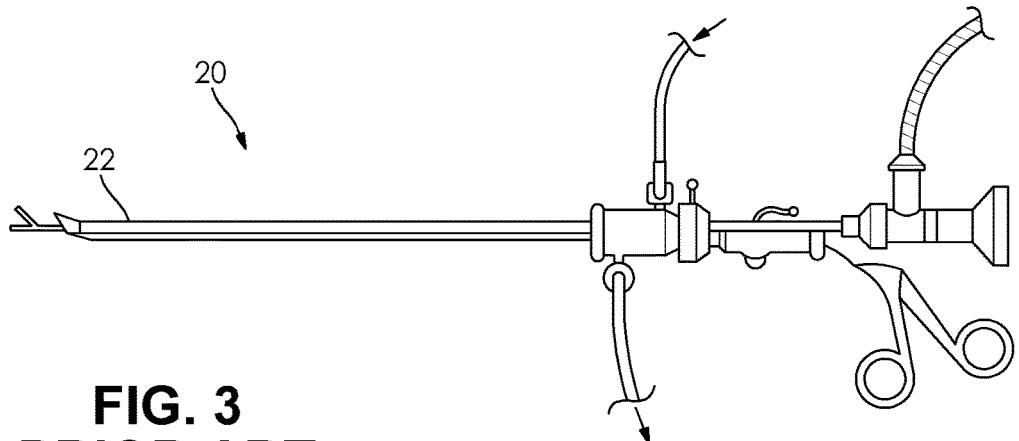
FIG. 3 is a schematic of a prior art hysteroscope suitable for deploying embodiments of the inventive catheters disclosed herein.

The present invention has utility in engaging the interior wall of the Fallopian tube and effectively removing cells therefrom for diagnostic purposes. A device and process is provided for collecting such cells in a minimally invasive procedure that in some embodiments occurs without cutaneous incision.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention It must be noted that as used herein and in the appended claims, the singular forms "a", "an", and "the" include plural referents unless the context clearly dictates otherwise. Thus, for example, reference to "a balloon" includes a plurality of such balloons and reference to "the channel" includes reference to one or more channels and equivalents thereof known to those skilled in the art, and so forth.

Embodiments of an inventive catheter for Fallopian tube diagnostics are provided for the performance of minimally invasive procedures including (1) Access to the proximal os of the Fallopian tube via an intrauterine approach; (2) Advance of an introducer catheter to cannulate and form a fluid tight seal with the proximal os; (3) Use of a second catheter inside the introducer catheter to track the length of the Fallopian tube and out into the abdominal cavity; (4) Inflation of a balloon at the end of the second catheter with retraction of the second catheter until the balloon seals the distal os of the Fallopian tube. Retraction of the second catheter produces contact with the intraluminal surface of the Fallopian tube to dislodge cells for improved sampling; and (5) and provisions to irrigate the Fallopian tube and recover the irrigation fluid for cytology or cell analysis.

Specific embodiments of an inventive catheter for Fallopian tube diagnostics are also provided for the performance of minimally invasive procedures including (1) Access to the proximal os of the Fallopian tube via an intrauterine approach; (2) Advance of an introducer catheter to cannulate the proximal os; (3) Use of a second catheter inside the introducer catheter to track inside the Fallopian tube; An inflated balloon at the end of the second catheter is advanced across the proximal portion of the Fallopian tube and is everted further into the Fallopian tube; (4) The balloon contacts the intraluminal surface of the Fallopian tube and dislodges cells for improved sampling; and (5) the balloon is removed and inserted into a vial for cell collection and subsequently processed Embodiments of the inventive catheter are configured to be inserted into the Fallopian tube, which is typically very difficult. The Fallopian tube is curved, and the soft tissue of the tube collapses, resulting in multiple constrictions as passage is attempted. This is particularly true of the uterotubal junction (UTJ), which is prone to perforation when medical instruments are inserted in the constriction that occurs approximately 1 cm distal to the proximal os (opening) of the Fallopian tube in the uterus. The UTJ also typically presents a downward bend with a lumen size at the constriction that may be as small as 0.3 mm or 0.5 mm, while the lumen size of the Fallopian tube adjacent to the uterotubal junction is approximately 1 mm.

In at least one embodiment of the present invention, an elongated balloon that is initially inverted into a catheter lumen is deployed. The balloon everts upon pressurization inside the catheter, and the unrolling mechanism of the eversion creates a path through the Fallopian tube, regardless of tortuosity or constriction in the Fallopian tube. The great majority of the length of the balloon should be substantially inelastic, such that the balloon does not substantially expand and dilate the Fallopian tube as it everts, preferably so the Fallopian tube does not expand or dilate as the balloon everts. Balloon expansion may burst or injure the Fallopian tube. However, the design also incorporates an elastic distal balloon end that expands to allow sealing of the distal os upon balloon retraction.

An inventive process common to the various embodiments of inventive devices includes the deployment of the distal end of a catheter. In some inventive embodiments, an inventive catheter distal end is delivered to a proximal end of the Fallopian tube with resort to a conventional hysteroscope. Regardless of the mode of deployment, a retracted portion of an inventive catheter is extended into contact with the interior wall of the Fallopian tube. It has been surprisingly found that the act of extending the portion abrades sufficient cells from the Fallopian tube wall to perform histological evaluation. This is observed for planar surfaces of seemingly non-abrasive character. While an abrasive is present on the tube contacting surfaces in some embodiments, such an abrasive is found not to be necessary. It has also been surprisingly found that withdrawal of the extended portion removes still more cells. In other inventive processes the extended portion is retracted prior to catheter removal so as to preclude dispersal of dislodged Fallopian tube cells to surrounding tissue. Upon catheter removal contacting the exposed portion, now covered in cells with a microscope slide or other diagnostic substrate, is sufficient to test for abnormal cells and in particular cancerous cells.

Referring now to the figures, in FIGS. 2A-2D an introduction catheter 10 with an inverted inelastic sleeve 12 and an attached distal elastic balloon 14 is (A) inserted through an introduction catheter 10 that resides in the working channel 22 of an operative hysteroscope 20 (FIG. 3), and used to cannulate the proximal os of the Fallopian tube 1; (B) inflated to evert the sleeve 12 the length of the Fallopian tube 1 and distend the distal elastic balloon 14; and (C) retracted slightly to seal the distal os 18 of the Fallopian tube 1 with the inflation of the elastic balloon 14 upon full advancement of the inverted elastic sleeve 12. FIG. 2D illustrates the introduction of saline to irrigate the length of the Fallopian tube 1 between the introducer catheter 10 and the everted sleeve 12 with the retraction of the inflated elastic balloon 14 that seals the opening of the distal os, and the subsequent collection of the irrigation fluid to obtain cell samples from substantially the entire length of the Fallopian tube 1 for cell analysis in the detection of ovarian cancer or other medical condition in FIG. 2D.

Figure 4:
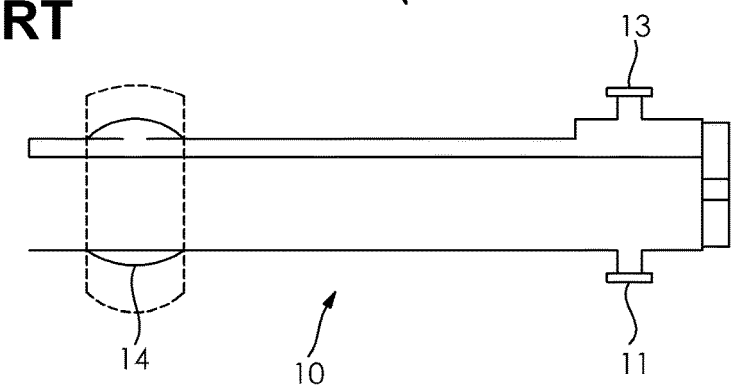
FIG. 4 is a schematic view of an embodiment of a proximal introducer catheter.

The catheter 10 described above, and in greater detail below may be introduced into the uterus of a patient using an operating hysteroscope 20, an example of which is shown in FIG. 3. An operating hysteroscope contains an endoscope and multiple channels; one channel may provide irrigation to distend the uterus and allow endoscopic visualization, and one or more additional channels 22 may allow instruments and/or catheters to be advanced distal to the hysteroscope. A Proximal Introducer Catheter 10 (see FIG. 2A and FIG. 4) may be advanced through the working channel of the operating hysteroscope, and used to cannulate the proximal os of a Fallopian tube. The balloon 14 on the proximal introducer catheter 10 is inflated to occlude the proximal os, and the everting balloon catheter is advanced through the proximal introducer catheter 10 into the proximal portion of the Fallopian tube. The sleeve/balloon element 14 is fully everted, and the inflated balloon tip pulled back to seal the distal os. Irrigation may be introduced via a port 11, and aspirated via the irrigation port 11 on the proximal introducer catheter 10, to collect the sample. Irrigation may also be introduced through both the everting balloon catheter and the proximal introducer catheter, followed by aspiration through one or both ports (11, 13).

Figure 5A:
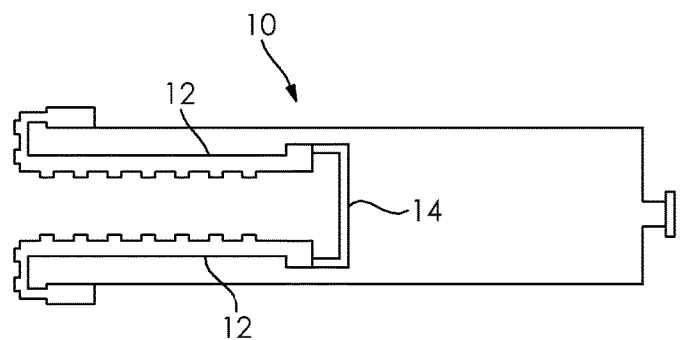
FIGS. 5A and 5B are schematic, cross-sectional views of an everting sleeve with a distal elastic balloon tip in a deflated state (A); and an inflated state (B)
Figure 5B:
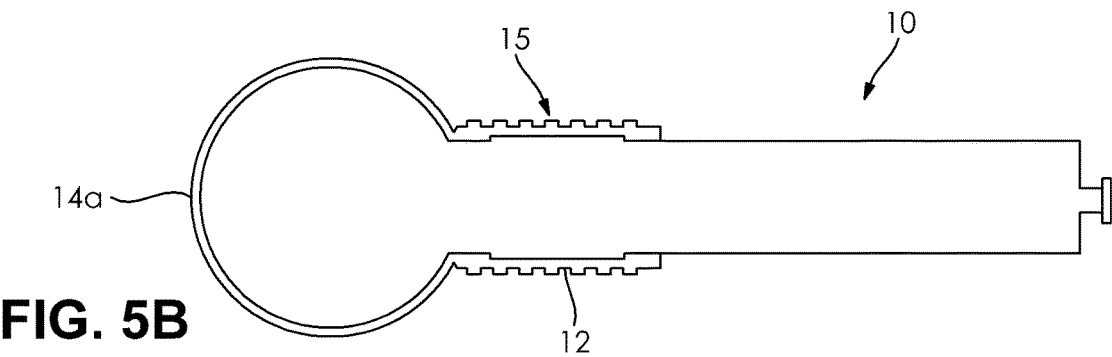

In inventive embodiments of the catheter, the sleeve 12 of the everting sleeve catheter is preferably a flexible, elongated, substantially inelastic tube with an elastic balloon tip 14 attached to its distal end, see FIGS. 5A and 5B. The inelastic tube 12 may have multiple ridges 15 along its length that extend externally of the tube when the tube has been extended/deployed, such as illustrated in FIG. 5B. Prior to deployment, the ridges extend inwardly, as the tube is inverted, as illustrated in FIG. 5A. With the ridges extending externally, as in FIG. 5B, the ridges are exposed to the luminal surface of the Fallopian tube when the sleeve is fully everted. These ridges increase the ability of the sleeve to gather cells upon balloon retraction. Alternatively, the outer surface of the everted inelastic tube may be covered with fabric or otherwise textured, to increase cell dislodgment during balloon retraction.

Figure 6A:
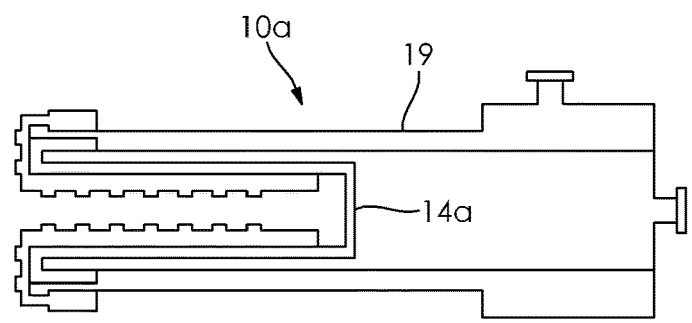
FIGS. 6A and 6B are schematic, cross-sectional views of an everting balloon with an outer construction sleeve in a deflated state (A); and an inflated state (B)
Figure 6B:
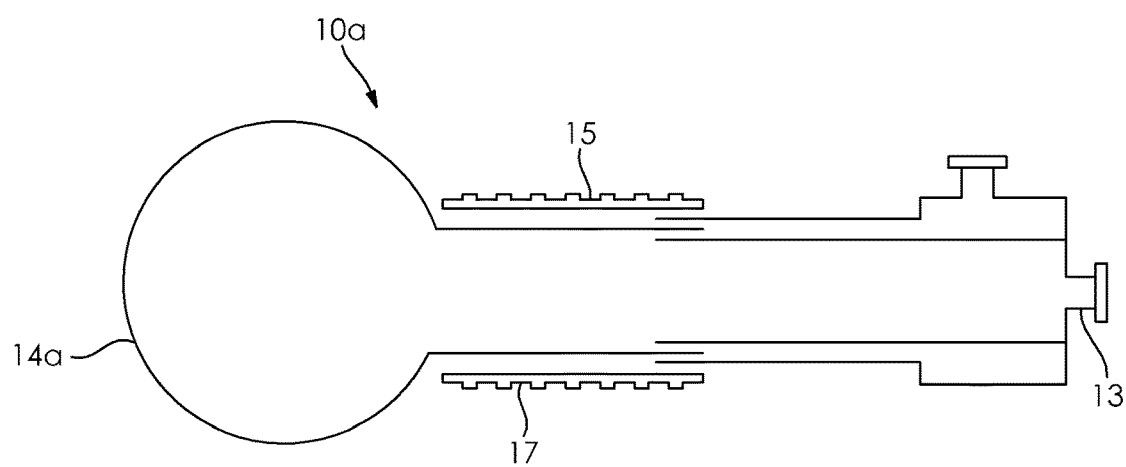
Figure 6C:
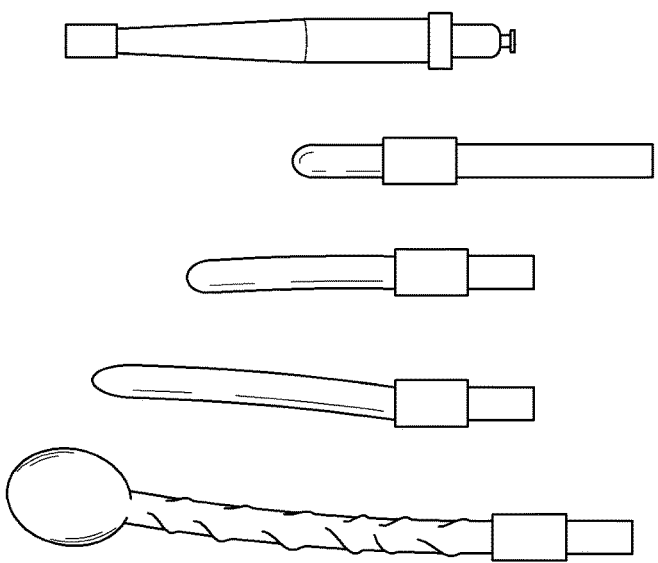
FIG. 6C is a series of photographs of an embodiment of the everting balloon with an outer construction sleeve.

FIGS. 6A-6C illustrate an embodiment of an everting sleeve catheter 10A which provides greater protection of the bond between the balloon and the sleeve of the everting sleeve catheter 10A during deployment, relative to that provided in the embodiment of FIGS. 5A and 5B. The construction of the embodiment of FIGS. 6A-6C involves attachment of an elongated, elastic balloon to the distal tip of the everting sleeve catheter. A substantially inelastic sleeve 17, slightly shorter in length than the elastic balloon 14, is attached to the elastic balloon 14 at the distal tip of the catheter, and inverted so that it lies inside the elastic balloon. Upon eversion of the balloon/sleeve combination 14A, the inelastic sleeve emerges from a double wall 19 of the catheter 10A, and lies on the outside of the elastic balloon and constricts the elastic balloon along the majority of its length, to prevent the elastic balloon from expanding and potentially rupturing the Fallopian tube during the time that the everting sleeve is being advanced through the Fallopian tube. Upon full balloon/sleeve eversion, the distal elastic balloon inflates to 3×-5× the diameter of the sleeve, for occlusion of the distal os upon retraction of the catheter with concomitant pullback of the inflated balloon. The catheter may contain a port 11 to allow irrigation to occur between the balloon and the outer sleeve, if desired.

Figure 7A:
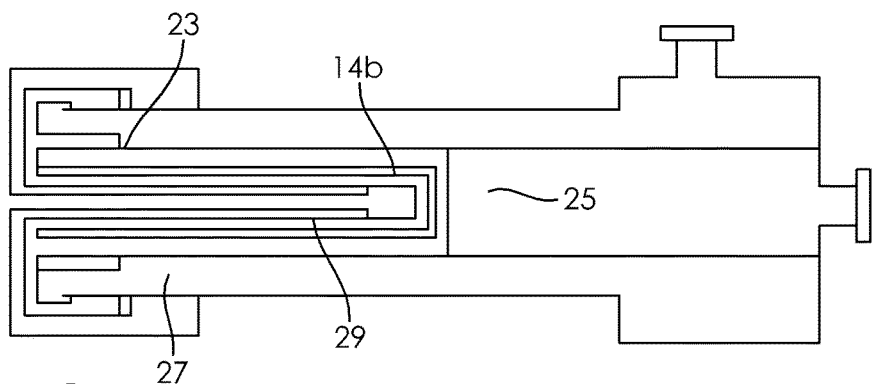
FIGS. 7A and 7B are schematic, cross-sectional views of an everting (sleeve and elastic balloon) with an inelastic delivery balloon in a deflated state (A); and an inflated state (B)
Figure 7B:
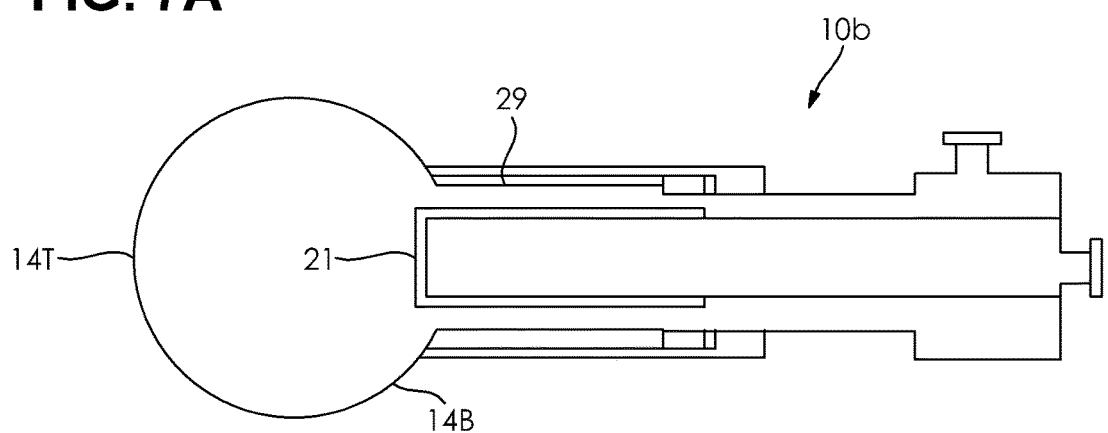
Figure 7C:
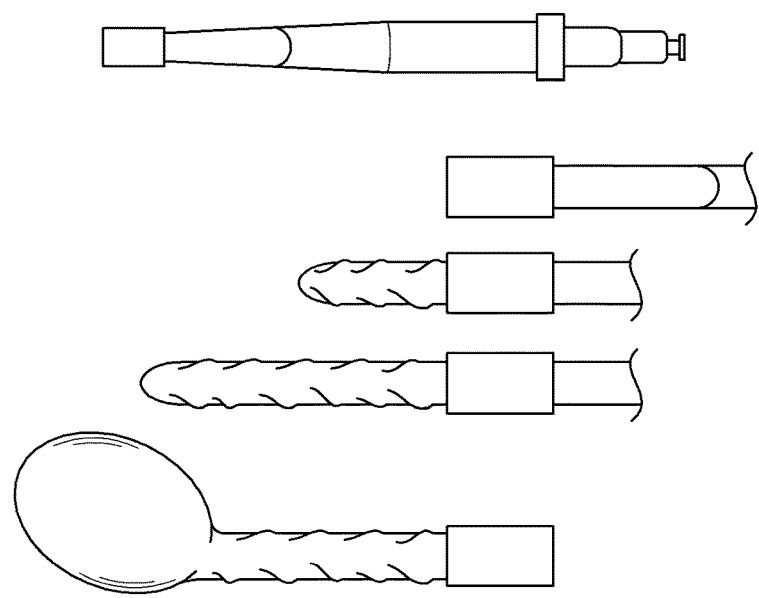
FIG. 7C is a series of photographs of an embodiment of the everting (sleeve and elastic balloon) with an inelastic delivery balloon.

FIGS. 7A-7C illustrate an embodiment of an everting sleeve catheter 10B where a concentric double walled catheter is provided, and the eversion of three layers are attached to the distal catheter tip: (1) an elongated inelastic balloon 21 is attached to the distal tip of the inner catheter 23, and the balloon lies within the inner catheter lumen 25; (2) an elongated elastic balloon 14B equal in length to the inelastic balloon 21 is attached to the distal tip of the outer wall 27 catheter 10B, and it resides inside the inelastic balloon 21; and (3) an inelastic sleeve 29 shorter in length than the elastic balloon 14B is attached to the distal tip of the outer catheter wall 27, and it lies inside the elastic balloon 14B. Pressurization of the inner catheter 23 everts the inelastic balloon 21, which delivers the elastic balloon 14B and outer constricting sleeve 29. Following full eversion of all three layers, pressurization between the walls of the inner catheter and outer catheter inflates the elastic balloon. The inelastic sleeve 29 constricts the elastic balloon 14B along the majority of its length, and the distal, un-constricted tip of the balloon 14T expands to form the occlusion element. The potential advantage of this design is a decrease in frictional characteristics during the eversion process. In this embodiment, the inelastic balloon 21 delivers the elastic balloon and constricting sleeve. The elastic balloon does not undergo expansion until it has been fully everted, and therefore does not increase friction with the wall of an everting sleeve during eversion, as in previous embodiments, which can be a significant advantage in facilitating deployment, particularly when working with small diameter catheters required for traversing the Fallopian tube.

Figure 8A:
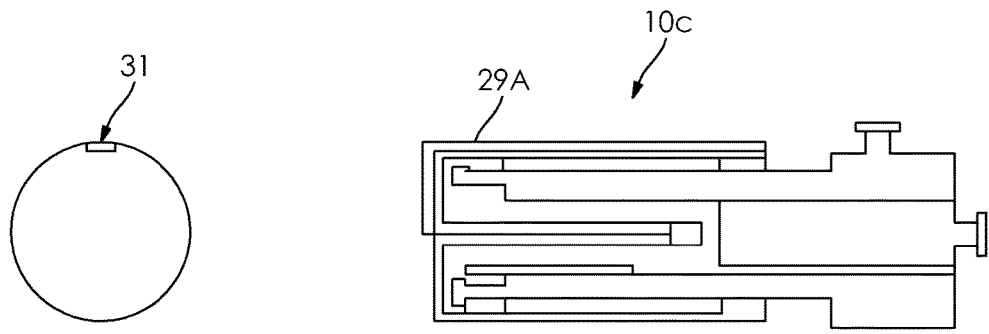
FIGS. 8A and 8B are schematic, cross-sectional views of an everting (sleeve and elastic balloon) with an irrigation lumen in a deflated state (A); and an inflated state (B)
Figure 8B:
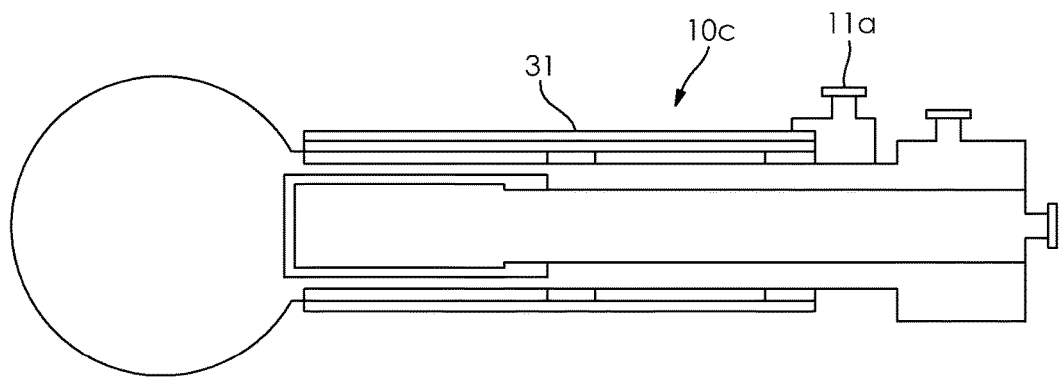
Figure 9A:
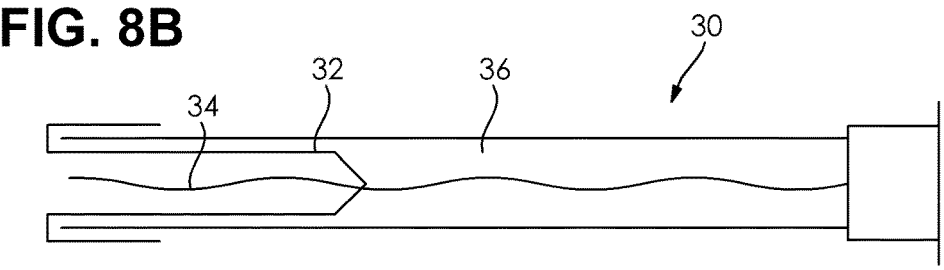
FIGS. 9A and 9B are schematic, cross-sectional views of an everting balloon catheter adapted for placement within an insertion catheter, the everting balloon catheter having a distal filament spiral, where distal is measured relative to the insertion point in a deflated state (A); and an inflated state (B)
Figure 9B:
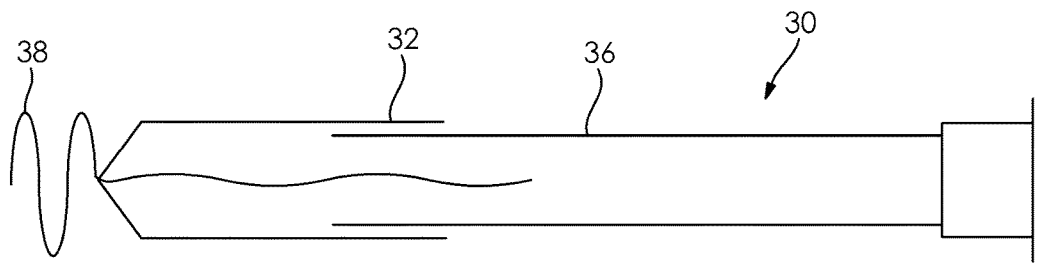
Figure 9C:
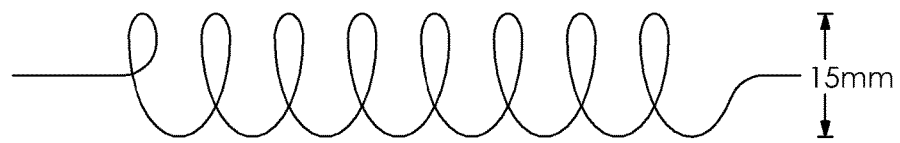
FIG. 9C is a photograph of an exemplary spiral filament with a diameter of 15 millimeters (MM)
Figure 9D:
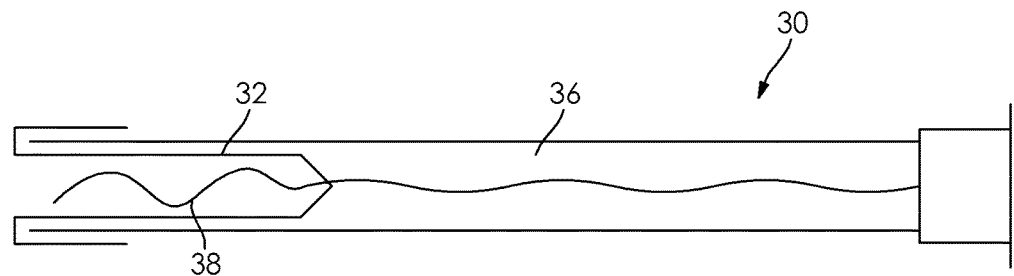
FIGS. 9D and 9E are schematic, cross-sectional views of an everting balloon catheter adapted for placement within an insertion catheter, the everting balloon catheter having a distal filament spiral heated sealed to the balloon, where distal is measured relative to the insertion point in a deflated state (D); and an inflated state (E)
Figure 9E:
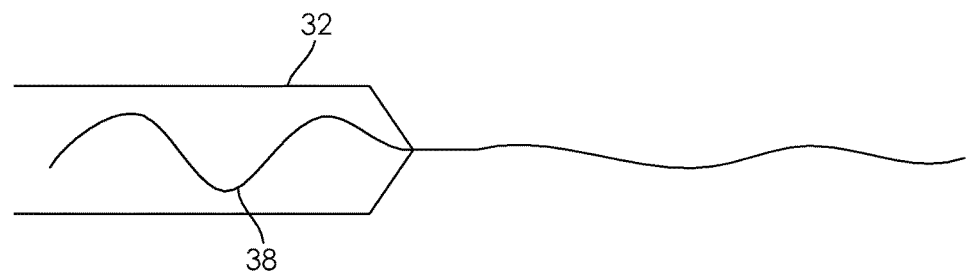
Figure 10:
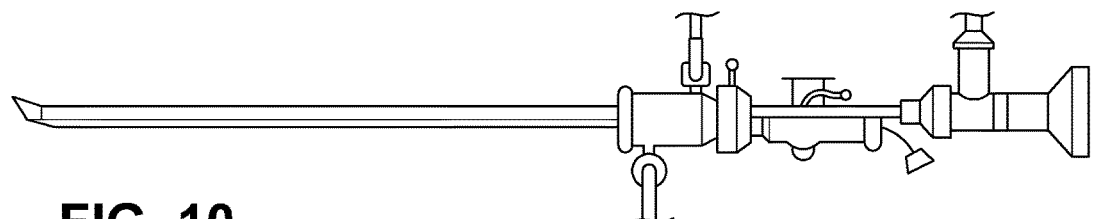
FIG. 10 is a side view of a prior art hysteroscope for deploying the catheters of FIGS. 8A-8E.
Figure 11A:
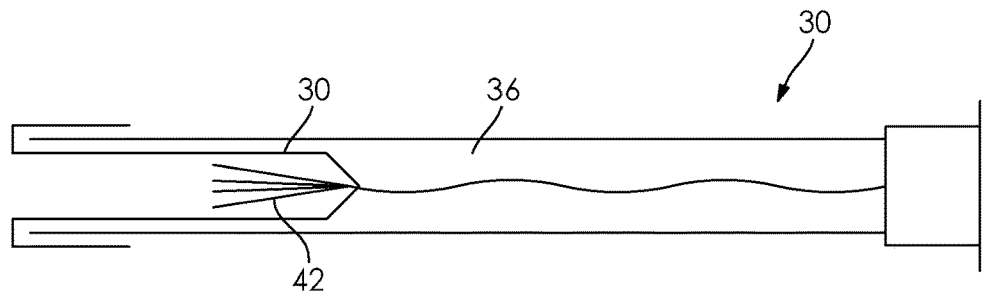
FIGS. 11A and 11B are schematic, cross-sectional views of an everting balloon catheter adapted for placement within an insertion catheter, the everting balloon catheter having a distal expanding brush, where distal is measured relative to the insertion point in a deflated state (A); and an inflated state (B)
Figure 11B:
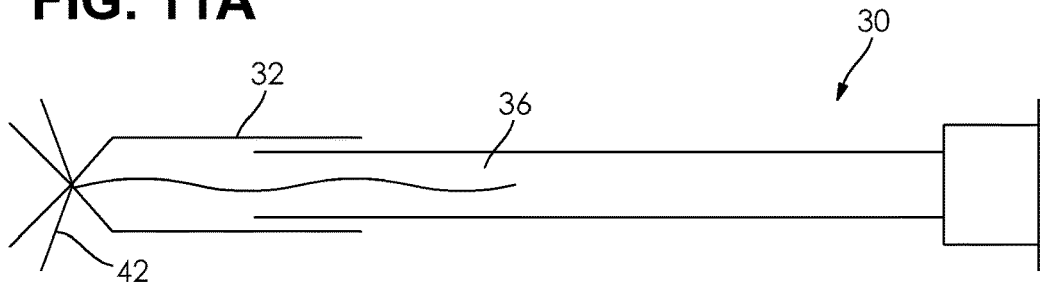

FIGS. 8A and 8B illustrate an embodiment of an everting sleeve catheter 10C with an inelastic sheath 29A that has a small lumen 31 for irrigation, with the lumen 29A connected to a third port 11A used for fluid irrigation and aspiration to obtain cytology samples.

Figure 12A:
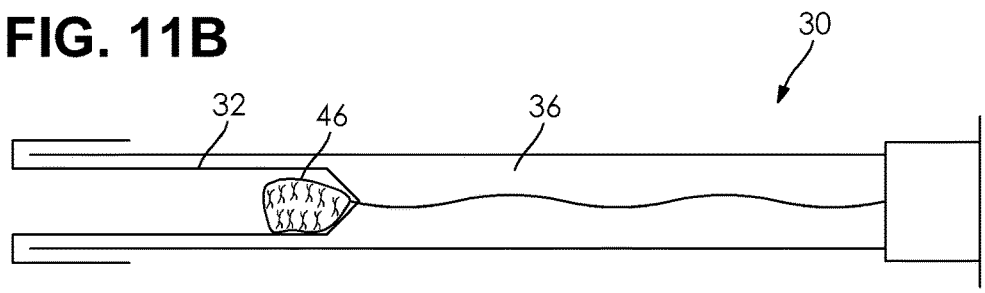
FIGS. 12A and 12B are schematic, cross-sectional views of an everting balloon catheter adapted for placement within an insertion catheter, the everting balloon catheter having a distal expanding foam, where distal is measured relative to the insertion point in a deflated state (A); and an inflated state (B)
Figure 12B:
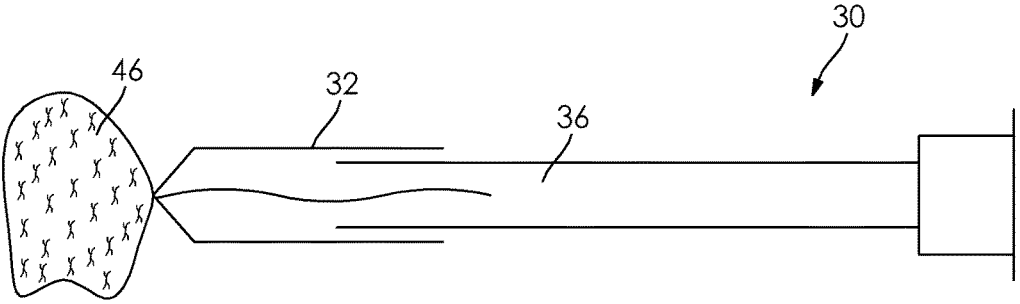

A modified design is shown in FIGS. 9A-9E. An elongated balloon 32 with an expandable member 34 attached to the distal end of the balloon 32 is inverted into the lumen 36 of a catheter 30. Upon inversion, the expandable member 34 lies inside the elongated balloon 32. In certain inventive embodiments, the expandable portion 34 is a spiral of multiple loops 38 of filament. The filament that forms the expandable member 34 is readily formed from a variety of materials illustratively including monofilament plastic material such as Nylon or polypropylene, fluoropolymers, or polylactic acid; metal such as stainless steel titanium, or platinum; or a superelastic metal such as Nitinol. In some embodiments a fiducial marker is present (not shown) to facilitate subsequent return to the situs of cell sampling. It is appreciated that the expanding portion may also have alternative configurations. For example, the expanding portion 34 may contain multiple outwardly oriented bristles 40 of plastic or metal (FIG. 18); or the expanding portion 34 is present as an elongated strand of material that curls 38, spreads or fans out 42, balls up 44 to a predetermined shaped when released from being constrained inside the catheter (FIGS. 11A-11B or FIGS. 14A-14B); or it may be compressed plastic foam that expands upon release into a wet environment (FIGS. 12A-12B). Upon pressurizing the catheter adjacent to the distal os, the balloon 32 everts so as to urge the inverted portion outward into the extended position and into contact with the Fallopian tube inner wall cells. In certain inventive embodiments, upon full balloon eversion, the extending portion 34 is delivered out of the distal os of the Fallopian tube, into the abdominal cavity. The extending portion 34 in some embodiments has to an outer diameter of approximately 15-20 mm.

Figure 18:
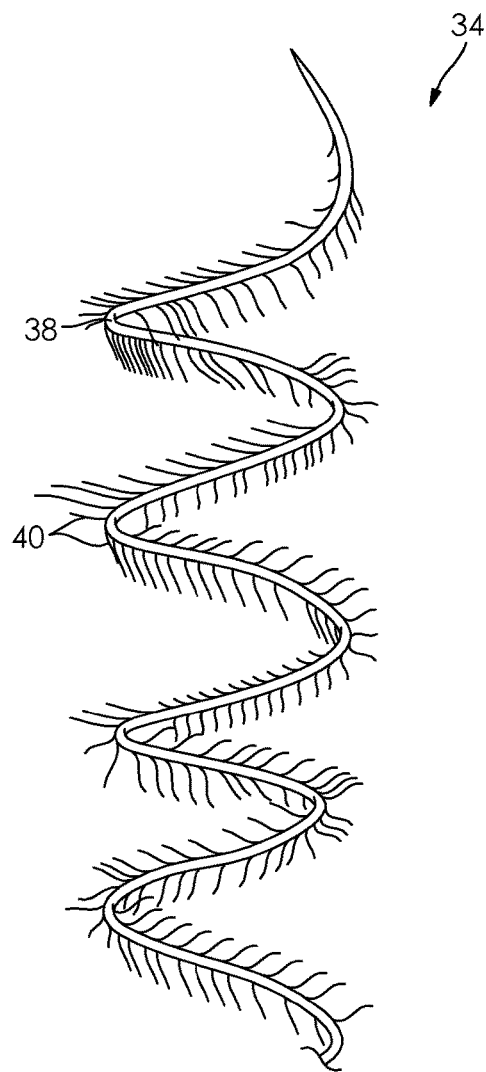
FIG. 18 is a photograph of a platinum coil wire having fibers extending therefrom and operative herein in the context of a catheter as depicted in FIGS. 9A-9E.
Figure 19:
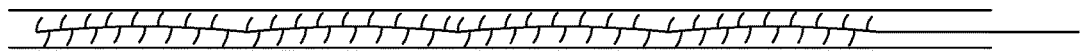
FIG. 19 is an illustration of a separate extending portion with the lumen of the catheter of FIG. 10.
Figure 20:
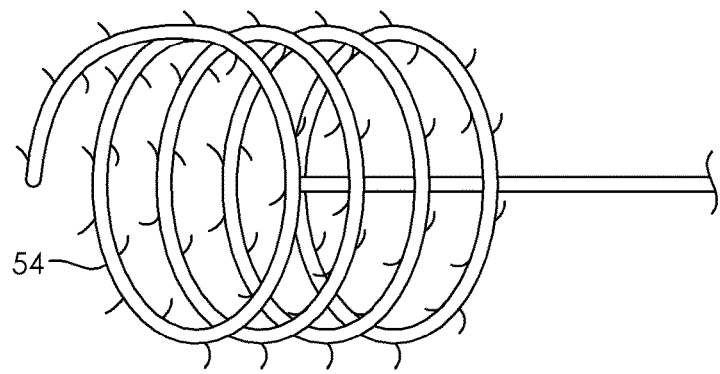
FIG. 20 is an illustration of the separate extending portion in deployed form beyond the orifice in the catheter of FIG. 10

An advantage of the extending portion 34 having multiple bristles is that there is a lot of surface area on which cells can be collected, including areas that are not likely to be exposed to shear forces when the device is pulled back in. This approach can maximize cell collection and minimize the amount of cells that are wiped off when the device is pulled through the Fallopian tube or into a sheath, as seen in FIGS. 18-20. In those embodiments in which the extending portion has greater surface area, the cell collection typically increases per linear unit of Fallopian tube so engaged under like pressurization conditions, as compared to a contourless extending portion.

Figure 13A:
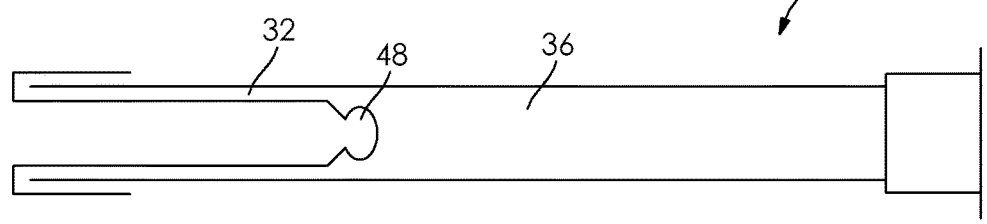
FIGS. 13A and 13B are schematic, cross-sectional views of an everting balloon catheter adapted for placement within an insertion catheter, the everting balloon catheter having a distal expanding inflated spherical balloon appendage, where distal is measured relative to the insertion point in a deflated state (A); and an inflated state (B)
Figure 13B:
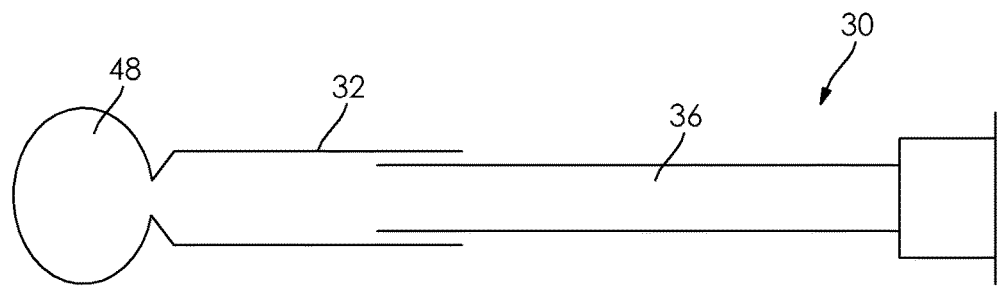
Figure 14A:
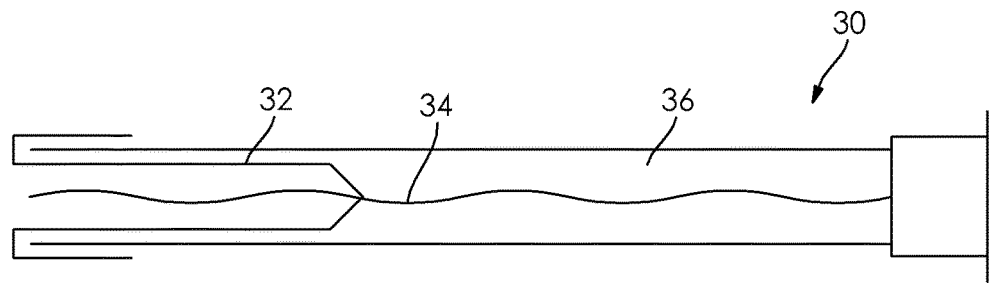
FIGS. 14A and 14B are schematic, cross-sectional views of an everting balloon catheter adapted for placement within an insertion catheter, the everting balloon catheter having a distal superelastic coil, where distal is measured relative to the insertion point in a deflated state (A); and an inflated state (B)
Figure 14B:
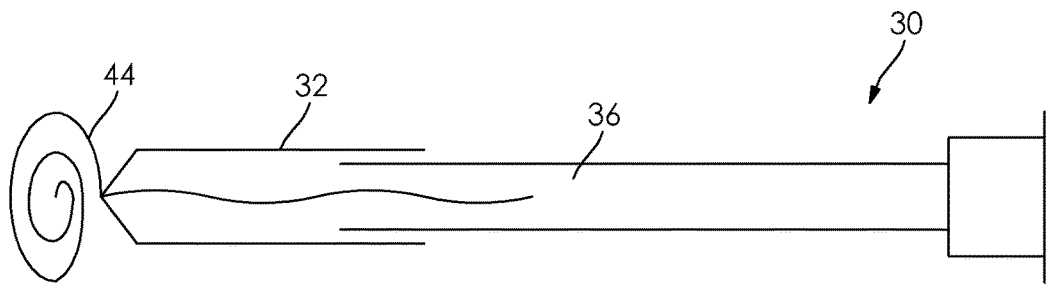
Figure 15A:
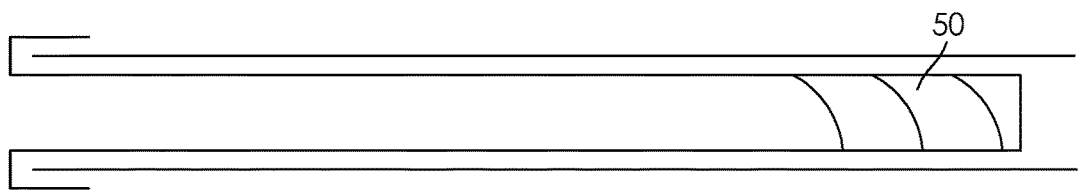
FIGS. 15A and 15B are schematic, cross-sectional views of an everting balloon spiral canula adapted for placement within an insertion catheter, the cannula having a distal expanding inflated spiral balloon appendage, where distal is measured relative to the insertion point in a deflated state (A); and an inflated state (B)
Figure 15B:
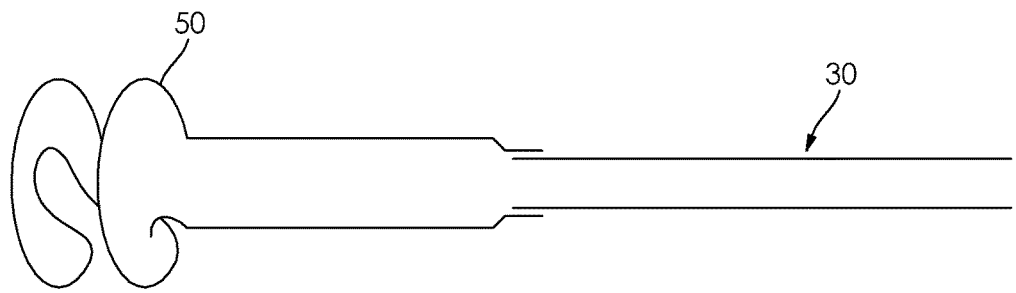
Figure 16A:
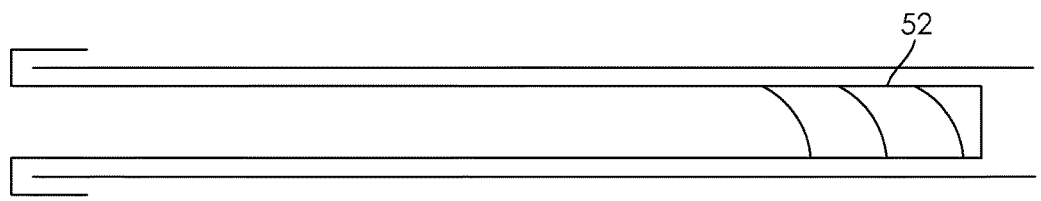
FIGS. 16A and 16B are schematic, cross-sectional views of an everting distal arc balloon cannula adapted for placement within an insertion catheter, where distal is measured relative to the insertion point in a deflated state (A); and an inflated state (B)
Figure 16B:
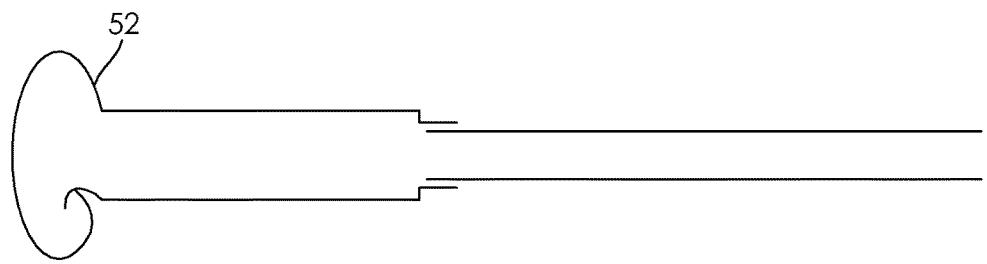

In still other embodiments of an inventive catheter, the extending portion, upon deployment defines: multiple filaments 42 attached to the distal end of the balloon 32 that splay out upon balloon eversion to form a brush 42 (FIGS. 11A-11B); a plastic foam structure 46 that is compressed inside the balloon 32 and expands on balloon 32 eversion and exposure to a fluid environment (FIGS. 12A-12B); an elastic or inelastic balloon 48 on the distal end of the inelastic sleeve balloon 32 (FIGS. 13A-13B), an everting balloon with a superelastic wire coil (FIGS. 14A-14B), a spiral everting balloon 50 (FIGS. 15A-15B), an everting distal arc balloon 52 FIGS. 16A-16B); or a long elastic filament of plastic or metal that gathers into a three-dimensional structure upon balloon eversion, such as an inner lumen 54 (FIGS. 17A-17B), and expanding portion 34 with multiple outwardly oriented bristles 40 (FIG. 18). It is appreciated that any of these embodiments of an inventive catheter extending portion are readily fitting with a fiducial marker that can be used to navigate back to the Fallopian tube as needed. Such markers are known to the art and illustratively include radio-opacity markers, isotopic markers, and radiofrequency markers. In still other embodiments, a biodegradable extending portion or a permanent extending portion are severed from the catheter. In still other embodiments, the extending portion delivers a therapeutic agent such as a chemotherapeutic drug, antibiotic, anti-inflammatory, or combinations thereof of the Fallopian tube tissue.

When the catheter is pulled into the working channel of the hysteroscope, cells are dislodged from the entire length of the inner surface of the Fallopian tube. In some embodiments, the extending portion is inverted through reduced the gas pressure with the balloon so as to shield collected cells with the catheter tip region internal bore (FIG. 19).

Without intending to be bound by a particular theory, the expanding portion creates friction between the outer surface of the expanding portion and the inner lining of the Fallopian tube sufficient to dislodge cells and adhere such cells to the expanding portion, even in certain instances on a contourless expanding portion. The expanded spiral at the distal end of the balloon contacts the fimbria at the distal end of the Fallopian tube, gathering cell samples as it is withdrawn. Since the Fallopian tube increases in inner diameter as it proceeds from its proximal to its distal end, the expanding portion ensures that cell samples are obtained at the distal end of the tube (fimbrial portion of the Fallopian tube). The elongated balloon and the distal expanding portion are in certain procedural embodiments retracted into the working channel of the hysteroscope, to avoid loss of cell samples as the hysteroscope is removed from the patient. An elastomer seal at the proximal end of the working channel of the hysteroscope seals against the outer surface of the catheter. A mark on the catheter body indicates the length of retraction necessary to ensure that the elongated balloon and distal spiral lay within the hysteroscope working channel. Upon removal of the hysteroscope from the patient, in some embodiments, a syringe containing saline solution is attached to the Luer fitting at the proximal end of the working channel, and the saline is used to flush cells gathered by the elongated balloon and expanding spiral into a test tube. It is appreciated that the cells decorating the extending portion are readily collected for testing by conventional techniques and are prepared for cytological, molecular or genetic examination.

Figure 17A:
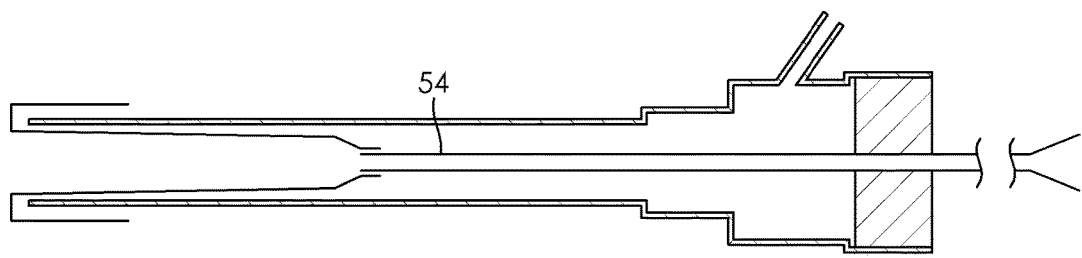
FIGS. 17A and 17B are schematic, cross-sectional views of an everting balloon catheter adapted for placement within an insertion catheter, the everting balloon catheter having a inner lumen that is pressuring to evert, where distal is measured relative to the insertion point in a deflated state (A); and an inflated state (B)
Figure 17B:
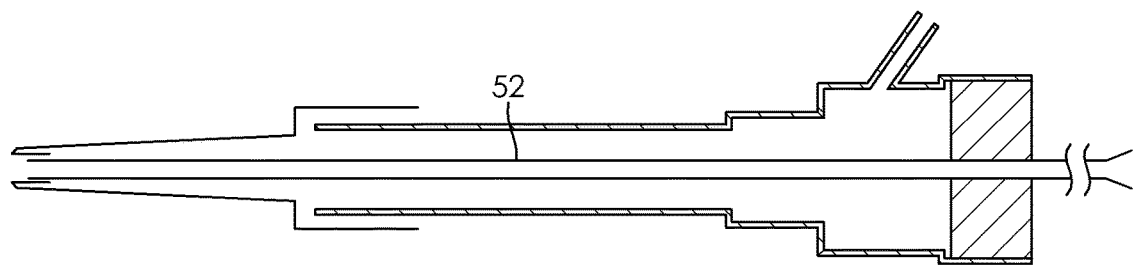

An alternative embodiment of that shown in FIGS. 17A-17B in which a coil is attached to the end of the inverting balloon, an inner lumen formed of the exemplary material polyethylene terephthalate (PET) is attached. The eversion process follows that of the aforementioned embodiments. This alternative embodiment also includes an inflation sideport and a proximal seal that allow the balloon to be inverted while maintaining an orifice through the inner lumen in fluid communication between the hysteroscope and the patient body tissue. Once everted, the inner lumen provides a pathway through which a separate extending portion is passed or a surgical instrument package is passed. An example of such a collection device is the spiral shown in FIG. 19 and FIG. 20. It is appreciated that cells can be collected from a specific portion of the Fallopian tubes, for example the fimbria, and then pulled back into the inner lumen so as to avoid the potential for distal cells to be wiped off by the inner surface of the proximal Fallopian tube as the device is removed.

Figure 21A:
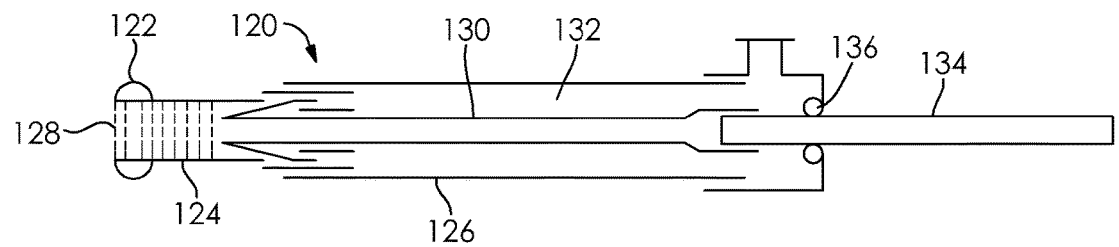
FIG. 21A is a schematic, cross-sectional side view that depicts a ball tip everting balloon catheter prior to deployment of the balloon through the hollow spring in accordance with embodiments of the invention.
Figure 21B:
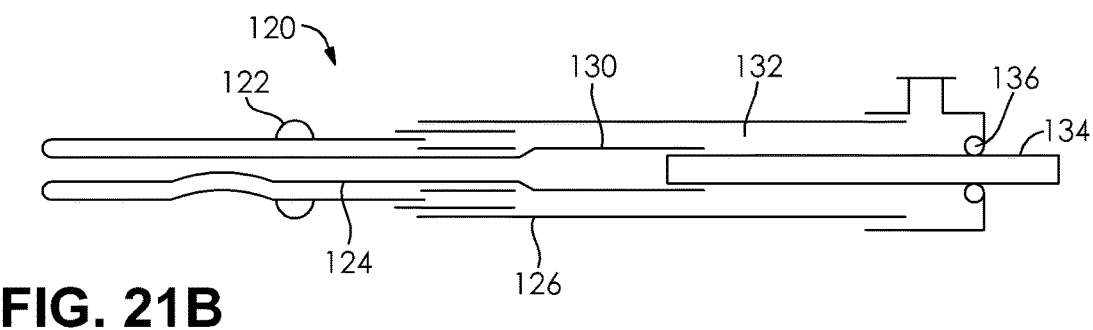
FIG. 21B is a schematic, cross-sectional side view that depicts a ball tip everting balloon catheter with the everted balloon through the hollow spring in accordance with embodiments of the invention.

FIGS. 21A and 21B are schematic, cross-sectional views of a ball tip everting balloon catheter 120 in accordance with at least one embodiment of the present invention. A spherical ball 122 is attached to the distal end of a spring tip 124 that is affixed to a catheter 126 and is provided to negotiate through a patient's UTJ without penetration through the UTJ sidewalls. The spring tip 124 and spherical ball 122 have an open lumen 128 that extends through the spring tip 124 and the spherical ball 122. The spherical ball 122 on the spring tip 124 is approximately 0.8-1.0 mm in diameter, and the hollow spring tip 124 has a length of approximately 1.5 cm, and an outer diameter of approximately 0.6 mm. The hollow spring tip 124 may be a metal (stainless steel or superelastic metal, e.g., Nitinol) coil spring sheathed on the outside with thin walled plastic heat shrink tubing, made of nylon, PET (polyethylene teraphthalate), or similar material. In a specific inventive embodiment, the spring tip 124 may be a metal coil spring co-extruded into a tubular plastic body. The hollow spring tip 124 may also be a flexible plastic tube, made of nylon, Polyethylene terephthalate (PET), polyether block amide (PEBAX), or similar materials. A long everting balloon 130 lies inside the hollow spring tip 124. The everting balloon 130 extends proximally inside the main lumen 132 of the introduction catheter 126 (a generally flexible tubular structure) or cannula (a generally rigid tubular structure), and the proximal end of the everting balloon 130 is attached to a push rod 134 that passes through a seal 136 on the proximal end of the catheter 126 or cannula. In operational use on a patient, the flexible ball tip 122 is manually advanced through the uterotubal junction. Once passage of the flexible ball tip 122 and spring tip 124 through the uterotubal junction is successful, the push rod 134 is advanced through the seal 136 of the previously pressurized introduction catheter 126 or cannula. Advancement of the push rod 134 causes a controlled eversion of the balloon 130 out of the hollow spring tip 124, through the length of the Fallopian tube.

In inventive embodiments, when the elongated balloon that is initially everted into a catheter lumen is deployed, the balloon everts upon pressurization inside the catheter, and the unrolling mechanism of the eversion tracks through the Fallopian tube, regardless of tortuosity or constriction in the Fallopian tube. The great majority of the length of the balloon should be substantially inelastic, such that the balloon does not substantially expand and dilate the Fallopian tube as it everts, preferably so the Fallopian tube does not expand or dilate as the balloon everts. Balloon expansion may burst or injure the Fallopian tube.

An inventive process common to the various embodiments of inventive devices includes the deployment of the distal end of a catheter. In some inventive embodiments, an inventive catheter distal end is delivered to a proximal end of the Fallopian tube with resort to a conventional hysteroscope. Regardless of the mode of deployment, a retracted portion of an inventive catheter is extended into contact with the interior wall of the Fallopian tube. It has been surprisingly found that the act of extending the portion abrades sufficient cells from the Fallopian tube wall to perform histological evaluation. This is observed for planar surfaces of seemingly non-abrasive character. While an abrasive is present on the tube contacting surfaces in some embodiments, such an abrasive is found not to be necessary. It has also been surprisingly found that withdrawal of the extended portion removes still more cells. In other inventive processes the extended portion is retracted prior to catheter removal so as to preclude dispersal of dislodged Fallopian tube cells to surrounding tissue. Upon catheter removal contacting the exposed portion, now covered in cells with a microscope slide or other diagnostic substrate, is sufficient to test for abnormal cells and in particular cancerous cells.

The catheter 126 described above, and in greater detail below may be introduced into the uterus of a patient using an operating hysteroscope 40, an example of which is shown in FIG. 3. An operating hysteroscope contains an endoscope and multiple channels; one channel may provide irrigation to distend the uterus and allow endoscopic visualization, and one or more additional channels may allow instruments and/or catheters to be advanced distal to the hysteroscope. The catheter 126 (see FIGS. 21A and 21B) may be advanced through the working channel of the operating hysteroscope, and used to cannulate the proximal os of a Fallopian tube. The everting balloon 130 is advanced through the proximal catheter 126 into the proximal portion of the Fallopian tube.

Figure 22A:
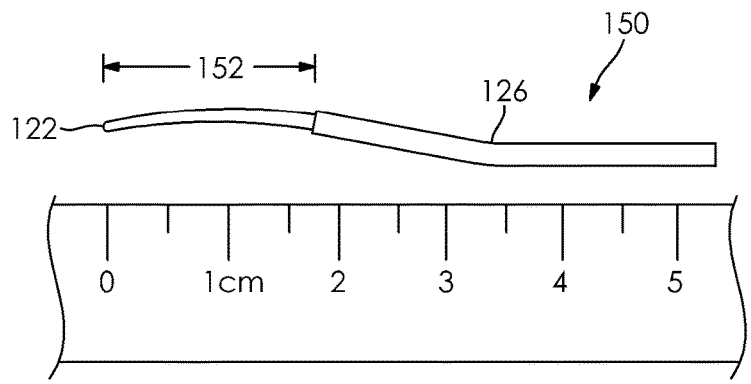
FIGS. 22A-22C are a series of photographs of the everting balloon exiting from a nylon flexible tip with a spherical ball in accordance with an embodiment of the invention.
Figure 22B:
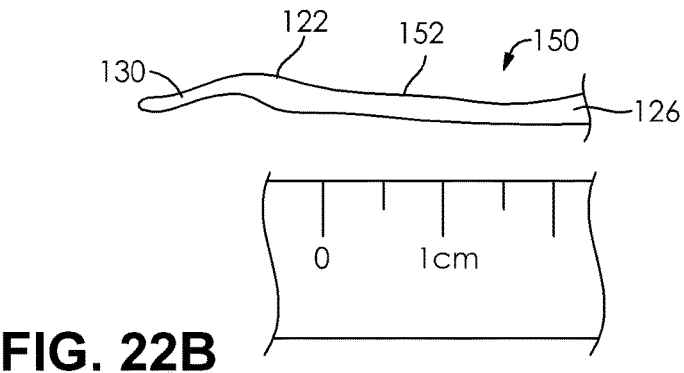
Figure 22C:
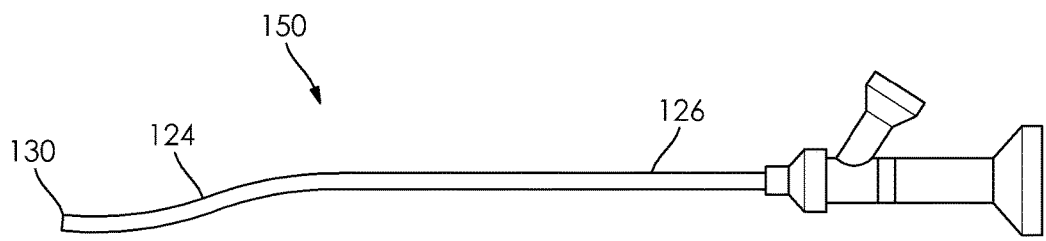

FIGS. 22A-22C are a series of photographs of the everting balloon 130 exiting from a nylon flexible tip 152 with a spherical ball 122 in accordance with an embodiment of the invention. The nylon flexible tip 152 and spherical ball 122 are configured to pass through the patient UTJ for the deployment of the everted balloon 130 in the Fallopian tube. In a specific inventive embodiment of the nylon ball tip everting balloon catheter 150 is configured with a 0.9 mm ball tip on 0.66 mm dia.×18 mm long nylon tip; 4 Fr catheter with a 0.64 mm dia. manual balloon that everts through and beyond the tip (24 atm).

Figure 23A:
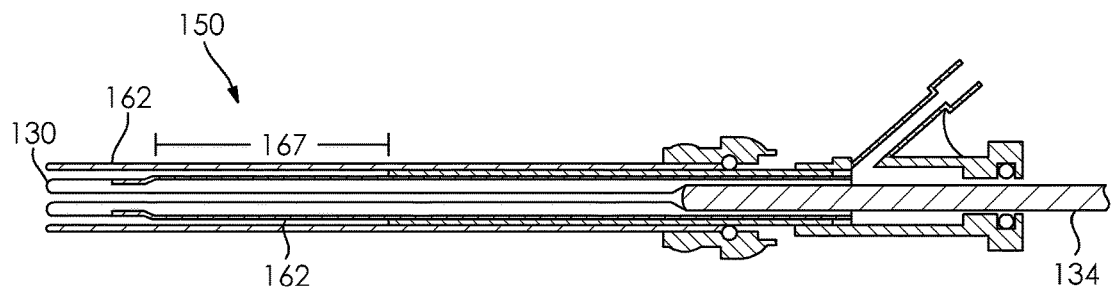
FIG. 23A is a schematic, cross-sectional side view that depicts a sheathed everted balloon tip catheter in accordance with an embodiment of the invention.
Figure 23B:
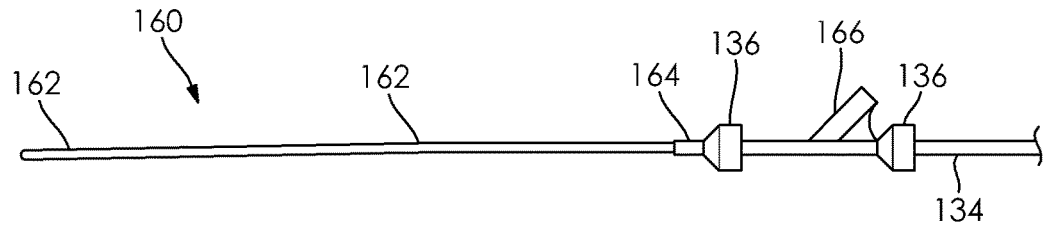
FIG. 23B is a photograph of the sheathed everted balloon tip catheter of FIG. 23A in accordance with an embodiment of the invention.

FIG. 23A is a schematic, cross-sectional side view that depicts a sheathed everted balloon tip catheter 160 or cannula, which is shown in the photograph of FIG. 23B, in accordance with an embodiment of the invention. A long inverted balloon 130, with an outer diameter of approximately 0.8-1.0 mm, is everted a length of approximately 1-3 cm, most preferably 1.2-1.5 cm out of the distal end of the catheter 126 or cannula. The balloon 130 is inflated with fluid to a pressure of approximately 14-24 atm (206-353 psi). The pressurized balloon 130 has a rounded end, a degree of flexibility along the balloon 130 length, while possessing sufficient column strength to allow the balloon 130 to be manually advanced through the uterotubal junction. In a specific embodiment, the balloon 130 is constructed of a thin-walled plastic material, such as polyethylene terephthalate (PET), polyethylene, Nylon, or a similar material, and the balloon 30 has a wall thickness of approximately 0.25 mil (0.00025"). The balloon may be an opaque color to enhance visibility during use. The length of the fully everted balloon 130 extends approximately 7 cm, such that when fully everted, the balloon 130 extends through the patient Fallopian tube, following the successful advancement of the 1.5 cm length of everted balloon through the uterotubal junction. Eversion of the balloon 130 is performed in a controlled manner, by advancing a push rod 134 through a fluid tight seal 136 at the proximal end of the catheter 126. At least a portion of the catheter 126 is preferred to be transparent (167), so that movement of the balloon 130 can be viewed through the hysteroscope through which the catheter is inserted, thereby providing the user with a direct view of the insertion procedure. The catheter 126 may be constructed of polymers such as Nylon (preferred), Pebax, polyurethane PET (polyethylene terephthalate), polyethylene, or polyvinyl chloride (PVC) plastic, with or without polymer or metal coil or braid reinforcement.

However, a balloon of the aforementioned dimensions when everted a 1.5 cm length out of the catheter 126 or cannula may not remain straight, rather the balloon 130 may assume a curved configuration, either a single "C" curve, or an "S" curve. However, it is difficult or nearly impossible to cannulate the proximal os of the Fallopian tube with a curved balloon, and to advance it through the uterotubal junction. The 1.5 cm length of everted balloon 130 may be straightened out by use of an outer plastic sheath 162 that lies coaxial to the catheter 126 or cannula, and covers the 1.5 cm everted balloon tip. At least a portion of sheath 162 is preferred to be transparent (167), so that movement of the balloon 130 can be viewed through the hysteroscope through which the catheter is inserted, thereby providing a user with a direct view of the insertion process. The sheath 162 may be constructed of polymers such as Nylon (preferred), Pebax, polyurethane, PET (polyethylene terephthalate), polyethylene, or polyvinyl chloride (PVC) plastic, with or without polymer or metal coil or braid reinforcement.

Figure 35:
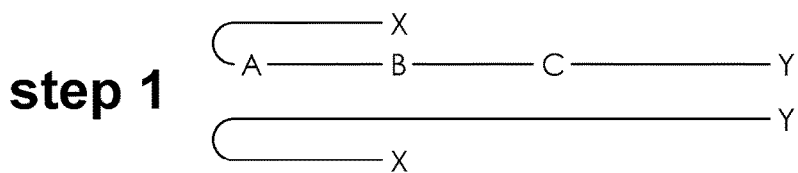
FIG. 35 illustrates the steps of eversion of a balloon used in embodiments of the invention.
Figure 35:
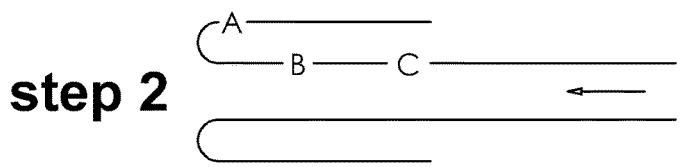
Figure 35:
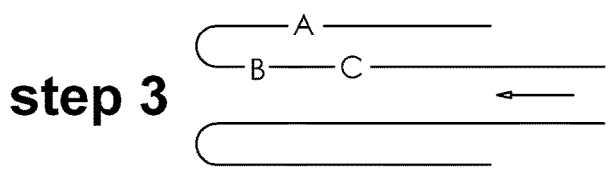

FIG. 35 illustrates the linear eversion of a deploying balloon. In the cross-section example of an everting balloon, one end of the balloon is fixed at point X and the other end can be moved at point Y. The balloon everts from the position shown in Step 1 to the position shown in Step 2 to the position shown in Step 3. In the inversion process, points A, B, and C move towards the left side of the diagram. As shown, as the balloon unrolls at the left side of the diagram, point A moves from the inside diameter of the balloon to the outside diameter. In practice, the balloon that has been everted during the preparation step is advanced into the proximal end of the Fallopian tube. Further eversion (extension) of the balloon (totaling up to 2-3 cm into the Fallopian tube) is accomplished by further rotation of the drive wheel 204. The balloon 130 is then deflated by relieving pressure in the inflation device. The balloon 130 is then retracted from the Fallopian tube. Because the Fallopian tube is a potential space, the Fallopian tube tissue collapses around the balloon. Because the balloon fills the Fallopian tube, the balloon surface area is equivalent to the surface area inside the Fallopian tube. This matched surface area optimizes tissue collection from the inside of the Fallopian tube.

To further optimize tissue collection, wrinkles may be added to the surface of the balloon, where the wrinkles form as the balloon deflates to create multiple edges, which also aid in cell collection. These edges work in a manner similar to the edges of the curette of the U-Scope predicate device and the edges of the jaws in the biopsy forceps predicate device. Similar to these features on the predicate devices, the edges formed by the wrinkled balloon focus the contact force on the anatomical wall in order to collect cells. Because the collection surface is a polymer balloon, however, the contact with the endothelium is less traumatic than the stainless steel contact surfaces of prior art diagnostic devices. The less traumatic nature of the wrinkles on the balloon for collecting cell tissue, allows for cycling of the inflation/deflation of the balloon inside the Fallopian tube to scrap cells free. The inventive balloon deployment device is then removed from the working channel of the hysteroscope and from the patient. Once the device is removed from the patient, cells can be removed from the balloon by dipping the balloon into a cytopreservative and stirring in order to agitate the cells. Alternatively, both balloon and sheath can be cut off and placed into a cytological preservative. In a specific embodiment a sheath may extend and deploy over the balloon as the balloon is deflated and removed to protect tissue samples that are now resident on the balloon surface.

Figure 24:
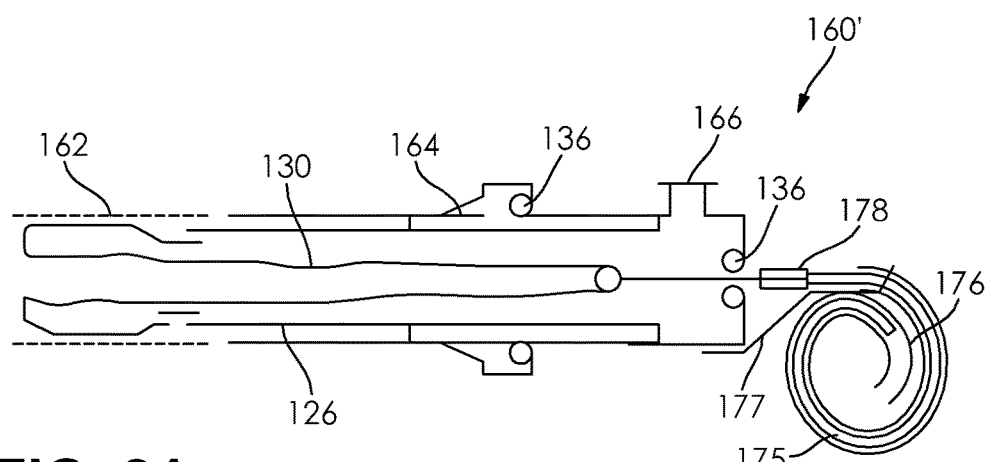
FIG. 24 is a schematic, cross-sectional side view that depicts a sheathed everted balloon tip catheter configured with a superelastic push rod and spiral carrier in accordance with embodiments of the invention.

FIG. 24 is a schematic, cross-sectional side view that depicts a sheathed everted balloon tip catheter 160' configured with a superelastic push rod 175 and spiral carrier 176 that eliminates the need to extend the push rod backwards for the full length of the push rod in accordance with embodiments of the invention. The push rod 175 is constructed of a superelastic material such as Nitinol (nickel-titanium compound) wire. The length of push rod 175 may then be coiled multiple times into a spiraling tubular carrier 176 made of polyethylene or polytetrafluoroethylene (Teflon). The outer spiral diameter of the carrier may be approximately 8 cm, rendering the proximal operating length much more compact. The plastic spiral carrier 176 may be attached to the proximal Tuohy-Borst fitting 136 on the catheter with a flexible strap 177 constructed of plastic or silicone rubber material. In a specific embodiment the superelastic push rod 175 has a diameter of approximately 0.025", and it is difficult to grip this wire and push it forward through the Tuohy-Borst seal 136. Therefore, a flexible grip 178 has been added, that slides freely on the push rod 175, but upon compression between the thumb and forefinger, provides excellent grip for push rod 175 advancement. The flexible grip 178 may be an elliptical cross-section frame made of polyvinyl chloride, silicone rubber, or similar flexible compound whose inner dimensions are approximately 2 cm in length, 1 cm in width, and 3 mm in height, with a wall thickness of approximately 2 mm. Holes in the proximal and distal faces of the grip are a slip fit with the push rod 175.

Figure 25:
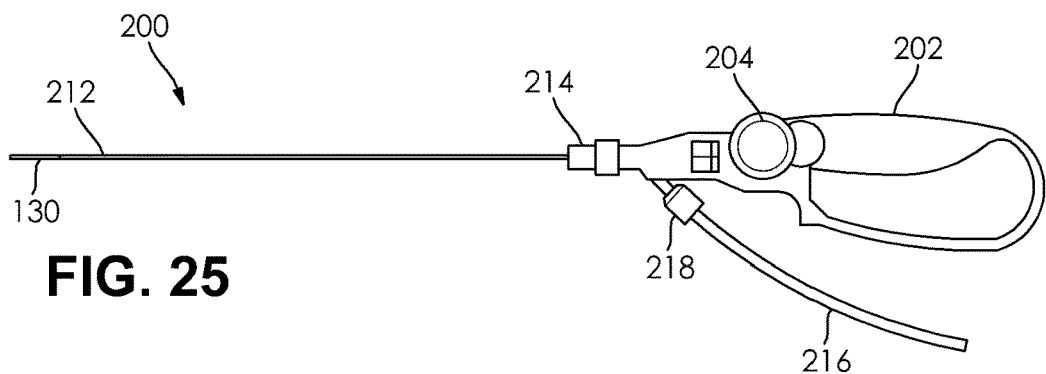
FIG. 25 is a side view that depicts a sheathed everted balloon tip catheter configured with a handle and drive wheel for advancing and retracting the balloon in accordance with embodiments of the invention.

FIG. 25 is a schematic side view that depicts an inventive embodiment of a sheathed everted balloon tip catheter 200 configured with handle 202. Handle 202 has a drive wheel 204 which advances and retracts the push wire 206 that causes the balloon 130 to evert linearly (gradually unfold from the inside out.). The drive wheel 204 may be made of plastic illustratively including ABS. The outer edge of the wheel may have notches to facilitate gripping the wheel during operation of the catheter 200. The top surface of the drive wheel 204 may have an arrow molded into it that indicates the correct direction in which to turn in order to evert the balloon. The opposite side of the drive wheel may have a square boss that inserts into a drive gear.

The catheter 200 holds the balloon 130 in a shaft 210 (which may be made up of a stainless steel tube and a Nylon tube), a sheath 212, and a sheath knob 214. The handle 202 also has an extension tube 216 that is attached to a luer 218 in the handle body. In order to enable balloon advancement, the balloon 130 and shaft 210 are pressurized with an inflation device (such as inflation device 172 of FIG. 23C) that is attached to the extension tube 216. Once the catheter device 200 is pressurized, a user rotates the drive wheel 204, which causes a push wire 206 to advance.

Figure 26A:
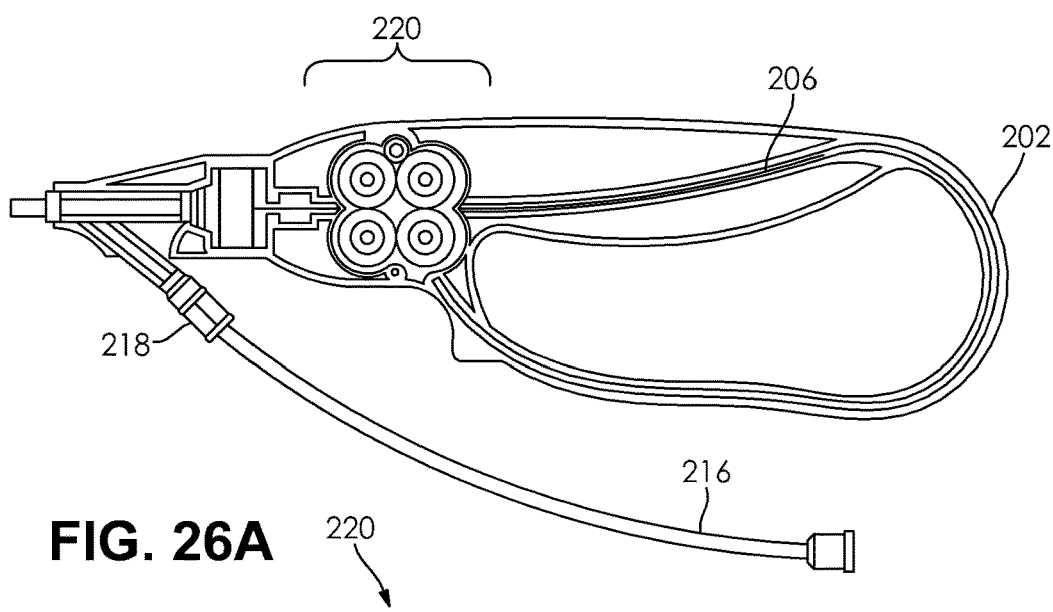
FIG. 26A is schematic, cross-sectional view of the handle portion of FIG. 25.
Figure 26B:
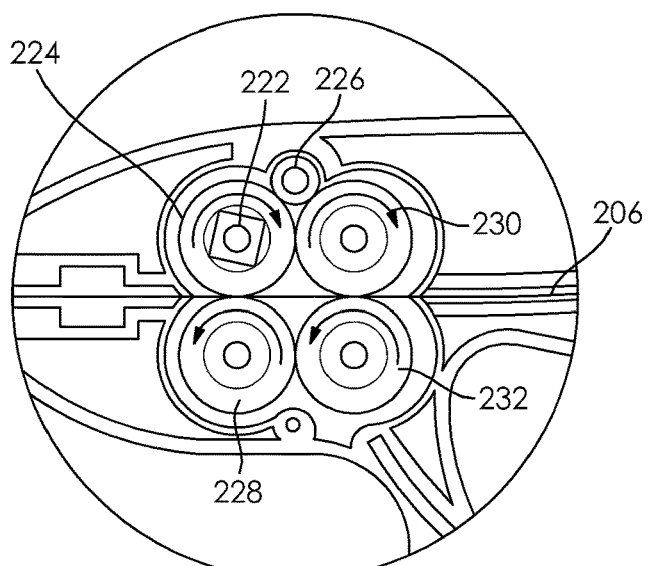
FIG. 26B is a detail view of the gear system in the handle portion as shown in FIG. 26A.

FIG. 26A is a cross-sectional view of the handle portion of FIG. 25, and FIG. 26B is a detail view that depicts the internal handle gear mechanism 220. The drive wheel drive wheel 204 has a square boss (not shown) that is inserted into square hole 222 in the drive gear 224. As the drive wheel 204 is rotated in a clockwise motion, the square boss causes drive gear 224 to spin. The drive gear 224 engages the idler gear 226 and gear one 228, causing these gears to spin. Likewise, the idler gear 80 causes gear two 230 and then gear three 232 to spin. The push wire 206 runs between rubber conduction surfaces on and between each of the four large gears (224, 228, 230, 232) and moves as shown in FIG. 26B during advancement of balloon 130. The balloon 130 advances until the proximal end of the push wire 206 passes between the drive gear 224 and gear one 228. The gear mechanism 220 allows for fine, precise, and controlled movement for the deployment and retraction of the balloon 130.

The sequence of steps used to enter and track through the Fallopian tube may be described with the embodiment of FIG. 23A. When it is desired to cross the uterotubal junction with the 15 mm length of everted balloon 130, the outer plastic sheath 162 is placed in apposition with the proximal os of the Fallopian tube, without entering the proximal os. The outer plastic sheath 162 supports the 15 mm length of everted balloon 130 until it enters the proximal os, The short length of pressurized everted balloon 130 that exits the supportive outer sheath 162 contains sufficient column strength to be manually advanced through the uterotubal junction, whereas an unsupported 15 mm length of everted balloon 130 does not contain sufficient rigidity by itself, and buckles upon attempted advancement through the proximal os and uterotubal junction.

The sheath 162 has an outer diameter of 5 Fr (1.59 mm), and the proximal end of the sheath 62 is attached to a male luer lock fitting 164 with a Tuohy-Borst seal 136 connector. A Tuohy-Borst adapter is a medical device used for creating seals between devices and attaching catheters to various other devices. The Touhy-Borst seal 36 is tightened down so that it has a slip fit with the catheter or cannula holding the sheath 162 in place thereby covering the everted balloon tip. The male luer lock fitting 164 may mate with a female luer lock fitting, if present, on the working channel of the hysteroscope. When these respective luer fittings are connected, the tip of the outer sheath protrudes approximately 2-3 cm out of the distal end of the hysteroscope. The outer sheath also protects the 1.5 cm everted balloon tip from injury as the catheter or cannula is advanced through the working channel of the metallic hysteroscope. A stainless steel tube of dimensions 0.050" OD×0.004" wall is preferred for the inner cannula 126, as it provides sufficient rigidity to prevent kinking of the portion protruding from the proximal end of the hysteroscope working channel.

Figure 23C:
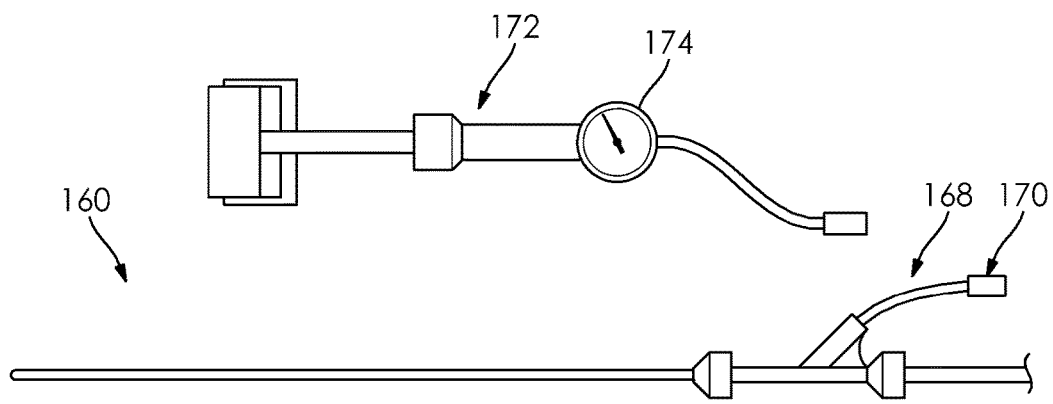
FIG. 23C is a photograph of the sheathed everted balloon tip catheter of FIG. 23A with a high pressure tubing reservoir and inflation device in accordance with an embodiment of the invention.

FIG. 23C is an image of the sheathed everted balloon tip catheter 160 of FIG. 23A with a high pressure tubing reservoir 168 and inflation device 172 in accordance with an embodiment of the invention. Pressurization of the balloon 130 using fluid injection may be performed using a threaded syringe device commonly known as an indeflator as the inflation device 172. Rotation of a threaded plunger shaft through a releasable lock increases and maintains pressure in the inflation device 172, while a pressure gauge 174 provided with the inflation device 172 allows control of input pressure. In a specific embodiment of the sheathed everted balloon tip catheter 160 provides for one person operation of the device. A length of high pressure tubing 168 is added between the inflation device 172 and the inflation port 166 on the device. The high pressure tubing 168 may be constructed of polymers such as polyurethane or polyvinyl chloride (PVC), with or without polymer or metal coil or braid reinforcement. The pressure tubing 168 contains an amount of intrinsic elasticity, while the everting balloon is generally inelastic. At full pressurization of the balloon 130, the pressure tubing 168 imparts fluid capacitance to the system. A small volume of fluid is contained in the everted balloon, and this volume is further subtracted by the volume occupied by the push rod 134 (which moves into the balloon 130 as it is being everted). The resultant everted balloon volume is small compared with the larger volume in the pressure tubing 168, which allows the balloon 130 to evert its full length without significant decrease in pressure, once the sheathed everted balloon tip catheter 160 has been pressurized. The stopcock valve 170 between the pressure tubing 168 and the inflation device 172 may be closed following pressurization, and the heavy inflation device 172 removed from the examination field, prior to insertion and eversion of the balloon 130. The less cumbersome, one operator procedure is the result of the design embodiment as shown in FIG. 23C.

As described above for FIGS. 23A-23C, the everting balloon 130 extends a total distance of approximately 7 cm distal to the tip of the catheter, in order to pass through the entire length of the Fallopian tube. The everting balloon 130 assumes a toroidal shape as it exits the catheter tip, and the everted portion possesses a double walled configuration. Thus, the push rod 134 must advance forward a distance of 14 cm in order to yield an everted balloon length of 7 cm. This length of push rod initially extends backwards from the proximal end of the catheter 126, directly into the face of the operator, making its use cumbersome. The length of the push rod 134 also makes the push rod susceptible to contamination of the sterile device, as the proximal end of the long push rod 314 may contact the physician's face or surgical mask during use. Therefore, it is desirable to provide a push rod system that does not have to extend backwards its full length. The superelastic push rod and carrier design of FIG. 24 and the sheathed everted balloon tip catheter 200 configured with handle 202 of FIG. 25 act to contain the push rod and avoids the need to extend the push rod back towards the user.

Figure 27:
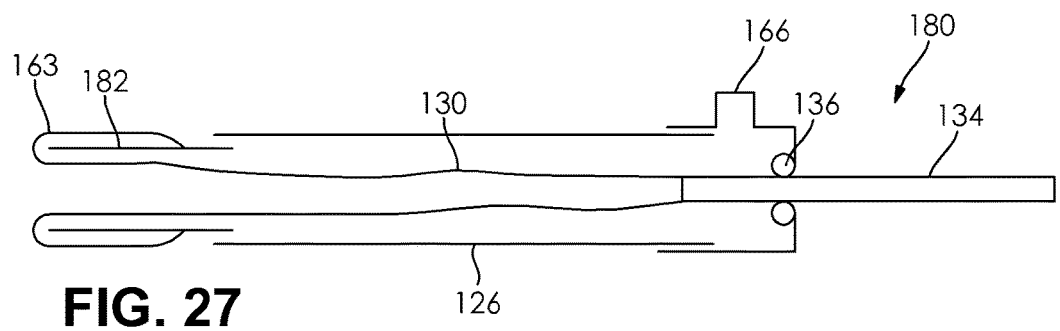
FIG. 27 is a schematic, cross-sectional side view that depicts an everted balloon tip catheter with a thin walled tube with a diameter smaller than the inflated diameter of the everting balloon for insertion into the patient's uterotubal junction in accordance with an embodiment of the invention.

FIG. 27 is a schematic, cross-sectional side view that depicts an everted balloon tip catheter 180 with a thin walled tube 182 with a diameter smaller than the inflated diameter of the everting balloon 130 for insertion into the patient's uterotubal junction in accordance with an embodiment of the invention. The thin walled tube 182 straightens a portion of the balloon tip 163. The thin walled tube 182 may have an approximately 0.0005"-0.001" wall thickness, and may extend 1.5 cm distal to the tip of the cannula. The thin walled tube extension 182 supports the balloon 130 and keeps the balloon tip 163 straight, but because thin walled tube diameter is smaller than the balloon diameter, this allows the balloon 130 to retain flexibility and compressibility, which are properties necessary to allow the balloon 130 to be advanced through the uterotubal junction. In a specific embodiment the balloon has a 0.040" (1 mm) OD with a 0.033" OD×0.001" wall×1.5 cm long inner tube to support and straighten the balloon.

Figure 28:
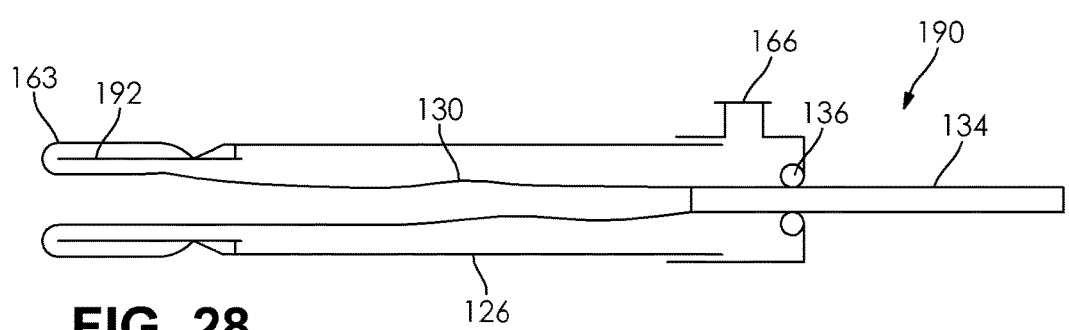
FIG. 28 is a schematic, cross-sectional side view that depicts an everted balloon tip catheter with one or more flexible plastic monofilament strands attached to the distal end of the cannula that extend into everting balloon tip for insertion into the patient's uterotubal junction in accordance with an embodiment of the invention.
Figures 29A, 29B, 29C:
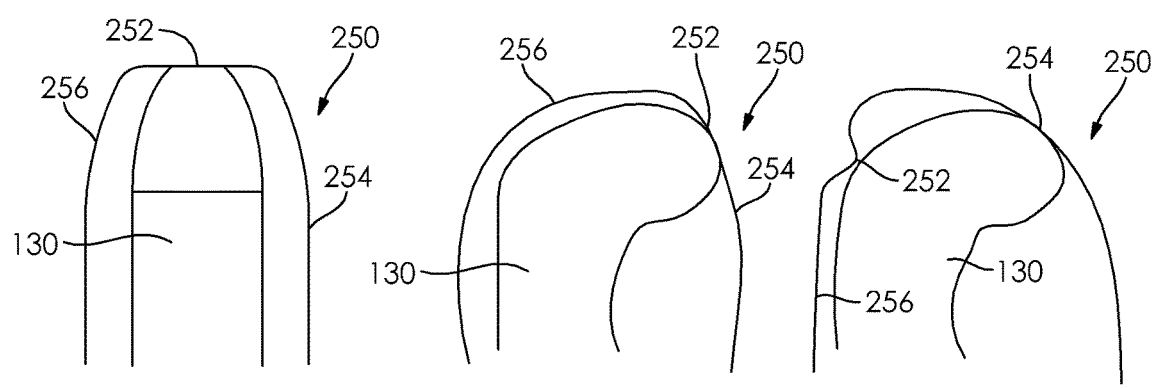
FIGS. 29A-29C are a series of side perspective views of a steerable balloon tips using guide wires in accordance with an embodiment of the invention.

FIG. 28 is a schematic, cross-sectional side view that depicts an everted balloon tip catheter 190 with one or more flexible plastic monofilament strands 192 attached to the distal end of the cannula 126 that extend into everting balloon tip 163, thereby supporting and keeping the tip straight for insertion into the patient's uterotubal junction in accordance with an embodiment of the invention. In a specific embodiment the one or more flexible plastic monofilament strands 192 extend 1.5 cm into the balloon tip 163. The monofilament may be formed of nylon, polypropylene, or other flexible plastic material. The monofilament strands may have a diameter of approximately 0.006"-0.012". In a specific embodiment the balloon has a 0.033" (.8 mm) OD with a 0.008" diameter nylon monofilament inside a 1.5 cm long everted balloon tip FIGS. 29A-29C are a series of side perspective views of a steerable balloon tip 252 for an everted balloon catheter 250 using guide wires in accordance with an embodiment of the invention. As shown in FIG. 29A a steerable balloon tip 252 is controlled by a right direction guide wire 254 and a left direction guide wire 256. In FIG. 29B the right guide wire 204 is pulled (as shown by the arrow) to steer the balloon 202 to the right. Conversely, in FIG. 29C the left guide wire 206 is pulled (as shown by the arrow) to steer the balloon 202 to the left. It is noted that additional guide wires may be added to provide movement in the Z-plane in addition to movement in the X-Y plane achieved with the pair of guide wires as shown.

Figure 30:
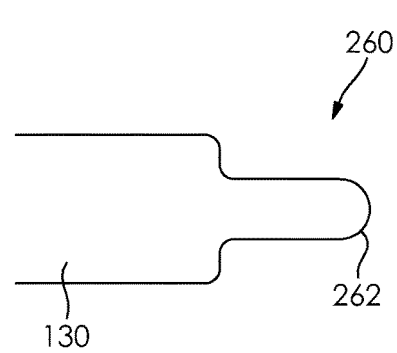
FIG. 30 is a side perspective view of a balloon catheter with a smaller diameter lead balloon tip in accordance with an embodiment of the invention.

FIG. 30 is a side perspective view of a balloon catheter 260 with a smaller diameter lead balloon tip 262 at the distal end of the everted balloon 130 in accordance with an embodiment of the invention. The smaller diameter lead balloon tip 262 is dimensioned so as to gradually expand the opening at the constriction presented by the patient uterotubal junction, as well be flexible with blunted edges so as not to perforate the walls at the uterotubal junction.

Figure 31:
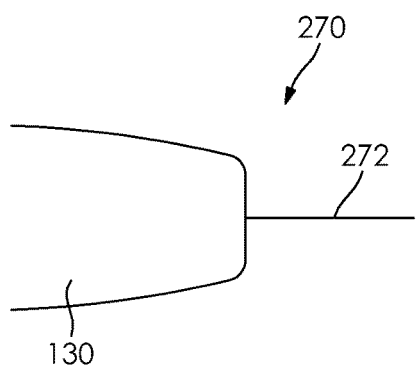
FIG. 31 is a side perspective view of a balloon catheter with a flexible guide wire on the tip of the balloon catheter in accordance with an embodiment of the invention.

FIG. 31 is a side perspective view of a balloon catheter 270 with a flexible guide wire 272 on the tip of the balloon 30 in accordance with an embodiment of the invention. The flexible guide wire leads the balloon catheter 220 through the patient uterotubal junction.

In embodiments of the inventive everted balloon catheters a portion of the everted balloon may be treated with flouropolymer, silicone, and like material coatings that lubricate the surface at the lead portion of embodiments of the balloon catheters enter the constricted portions of the Fallopian tube.

Figure 32:
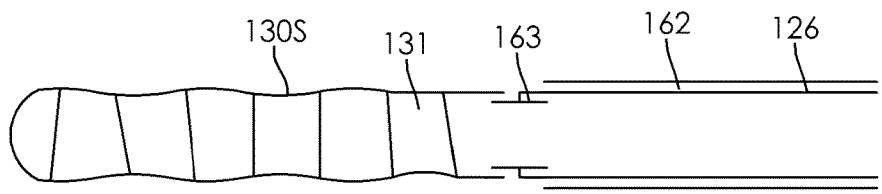
FIG. 32 is partial side perspective view of a balloon catheter prior to inversion of the striped balloon into the catheter or cannula of FIG. 12 in accordance with an embodiment of the invention.

FIG. 32 is partial side perspective view of a striped balloon 130S prior to inversion of the striped balloon 130S into the catheter or cannula of FIG. 32 in accordance with an embodiment of the invention. The indicia 131 on the balloon provide a visual feedback indicator of the progress of the balloon eversion. In a specific embodiment, the indicia 131 may be approximately 1 mm wide and spaced at approximately 1 cm increments along the entire length of the balloon 130S. Alternative spacing of the strips or other visual markers on the balloon may be spaced closer together for finer positional feedback, or further apart for coarser feedback. Other visual markers of length of eversion include a sinusoidal indicia with a known length of periodicity. It is also appreciated that indicia of length also include differently colorized segments of a known length.

Figure 33:
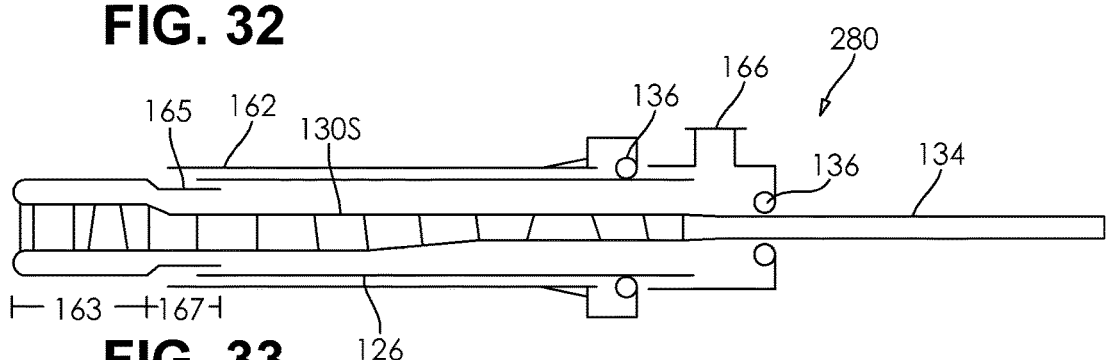
FIG. 33 is a schematic, cross-sectional side view that depicts a sheathed everted balloon tip catheter in accordance with an embodiment of the invention.

FIG. 33 is a schematic, cross-sectional side view that depicts a sheathed everted balloon tip catheter 280 configured with striped balloon 130S in accordance with an embodiment of the invention. As shown in FIG. 33 the indicia 131 of the striped everting balloon 130S are coupled with a transparent distal section 167 of the cannula or catheter 126 to provide visual feedback of balloon eversion.

In a specific embodiment the indicia 131 may be approximately 1 mm wide, spaced approximately in 1 cm increments along the entire length of the balloon and be pad printed or scribed with an indelible marker in a highly visible color. Pad printing (also called tampography) is a printing process that can transfer a 2-D image onto a 3-D object. Other patterns may be used instead of, or in addition to indicia 131 on the surface of the balloon 130S. For example, indicia 131 on the balloon 130S may be spaced 10 cm apart, and dots added in the remaining intervals between the indicia. Each indicia 131 that comes into view in the transparent distal section 167 indicates a successful eversion of a 5 cm length of balloon, as the push rod must be advanced a 10 cm length for a corresponding 5 cm of balloon eversion. Indicia of different thicknesses may be used, as well as different colored indicia, or a different number of indicia, in the same fashion described for the stripe and dot combination. In a specific embodiment color coded sections may be added to the balloon to indicate the extent of the balloon eversion.

Figure 34:
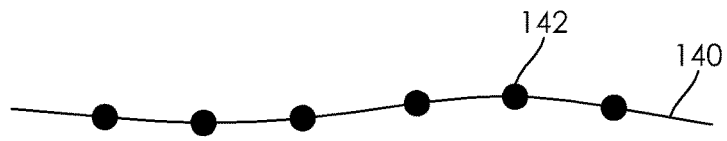
FIG. 34 is a side perspective view of a string with a series of knots or sutures in accordance with an embodiment of the invention.

Additional inventive embodiments of feedback markers, which are externally visible to the physician on the outside of the patient's body, for the extent of positive balloon eversion may include the use of a knotted string or sutures that may be spaced in known increments to provide tactile feedback as to the balloon eversion progress. The knots or sutures may be radio opaque. The string may have color coded zones for providing feedback to the operator. FIG. 34 illustrates a string 140 with a series of knots or sutures 142 in accordance with an embodiment of the invention. The balloon 130 may be transparent to enhance visibility of string, knots, or sutures. In a specific embodiment the knots or sutures may also provide an additional cell collection surface.

Further inventive feedback mechanisms may include ultrasound saline—air marking, and a sinusoidal pattern for the balloon, where the distances between maximums of a sinusoidal wave define an incremental distance of balloon eversion.

Any patents or publications mentioned in this specification are herein incorporated by reference to the same extent as if each individual publication was specifically and individually indicated to be incorporated by reference. The foregoing description is illustrative of particular embodiments of the invention, but is not meant to be a limitation upon the practice thereof.

The invention claimed is:

1. A process of collecting cells from a tissue surface of a Fallopian tube in a subject comprising:
deploying a distal end of a catheter at a proximal end of the tissue surface of the Fallopian tube;
everting an inelastic balloon extendible from the distal end of the catheter to contact the tissue surface of the Fallopian tube wherein in response to everting, over-expansion of the Fallopian tube by the inelastic balloon is prevented;
partially deflating said balloon to form wrinkles on an outer surface of said balloon and capturing the cells on said wrinkles;
and withdrawing said balloon from the subject to collect the cells from the Fallopian tube.

2. The process of claim 1 further comprising shielding the cells from a surrounding environment during said withdrawing.

3. The process of claim 1 wherein said everting further comprises two or more cycles of inflation and deflation of said balloon while positioned in contact with the tissue surface.

4. The process of claim 1 wherein the catheter is deployed through an insertion of a hysteroscope.

5. The process of claim 1 further comprising placing a fiducial marker on or in a target tissue of the tissue surface during said everting.

6. The process of claim 1 wherein the catheter, or the balloon, or both, does not perforate an anatomical structure defined by the tissue surface.

7. The process of claim 1 further comprising said balloon delivering a therapeutic agent into contact with the tissue surface.

8. The method according to claim 1, further comprising extending a filament in the Fallopian tube for cell collection.

9. A method for Fallopian tube diagnostics, comprising:
deploying a distal end of a catheter at a proximal end of the Fallopian tube;
pressurizing an inelastic balloon disposed in a first inverted position, the balloon having a rounded distal end at the distal end of the catheter;
advancing the rounded distal end of the balloon into the Fallopian tube by eversion, such that an inner diameter of the balloon in the first inverted position unrolls in the Fallopian tube at the rounded end to a second everted position, thereby forming an outer diameter of the balloon;
and contacting the outer diameter of the balloon to an inner diameter of the Fallopian tube for cell collection;
wherein in response to moving between the first inverted position and the second everted position, over-expansion of the Fallopian tube by the inelastic balloon is prevented.

10. The method according to claim 9, further comprising delivering a therapeutic agent by the balloon to the Fallopian tube.

11. The method according to claim 9, further comprising placing a fiducial marker at a target tissue along the inner diameter of the Fallopian tube during eversion.

12. The method according to claim 9, further comprising extending a filament in the Fallopian tube for cell collection.

13. A method for Fallopian tube diagnostics, comprising:
deploying a distal end of a catheter at a proximal end of the Fallopian tube;
pressurizing a balloon disposed in a first inverted position;
advancing the balloon into the Fallopian tube by eversion, such that an inner diameter of the balloon in the first inverted position unrolls in the Fallopian tube to a second everted position, thereby forming an outer diameter of the balloon;
and extending a filament into the Fallopian tube, the filament having a first configuration when the balloon is in the first inverted position, and a second configuration when the balloon is in the second everted position;
wherein the balloon is inelastic, such that in response to moving between the first inverted position and the second everted position, over-expansion of the Fallopian tube by the inelastic balloon is prevented.

14. The method according to claim 13, further comprising contacting the outer diameter of the balloon, the filament, or both, to an inner diameter of the Fallopian tube for cell collection.

15. The method according to claim 13, wherein the filament is configured to curl, spread, fan, ball-up, or expand-out, or combinations thereof, in response to the balloon moving between the first inverted position and the second everted position.

16. The method according to claim 13, wherein the filament is plurality of filaments.

\* \* \* \* \*